(12) United States Patent
Yoshida et al.

(10) Patent No.: US 10,265,053 B2
(45) Date of Patent: Apr. 23, 2019

(54) ULTRASONIC DIAGNOSTIC APPARATUS AND METHOD OF GENERATING ULTRASONIC IMAGE

(75) Inventors: Tetsuya Yoshida, Nasushiobara (JP); Naohisa Kamiyama, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 1333 days.

(21) Appl. No.: 11/928,803

(22) Filed: Oct. 30, 2007

(65) Prior Publication Data

US 2008/0262354 A1 Oct. 23, 2008

Related U.S. Application Data

(63) Continuation of application No. PCT/JP2007/050176, filed on Jan. 10, 2007.

(30) Foreign Application Priority Data

Jan. 10, 2006 (JP) .................................. 2006-002661
May 19, 2006 (JP) .................................. 2006-140283

(51) Int. Cl.
*A61B 8/00* (2006.01)
*A61B 8/08* (2006.01)
(Continued)

(52) U.S. Cl.
CPC .............. *A61B 8/469* (2013.01); *A61B 8/481* (2013.01); *A61B 8/483* (2013.01); *A61B 8/5238* (2013.01);
(Continued)

(58) Field of Classification Search
CPC ........... A61B 8/00; A61B 8/466; A61B 6/463; A61B 6/466; A61B 8/469; A61B 8/481;
(Continued)

(56) References Cited

U.S. PATENT DOCUMENTS 5,806,521 A * 9/1998 Morimoto ............ A61B 8/0858
600/447
5,873,830 A 2/1999 Hossack et al.
(Continued)

FOREIGN PATENT DOCUMENTS

JP 2-191444 7/1990
JP 5-168626 7/1993
(Continued)

OTHER PUBLICATIONS

Mutsumi Nishida, et al., "New Approach to Detecting Cervical Lymph Node Metastasis Using Contrast-Enhanced Ultrasound: Micro Flow Imaging with Levovist", Bisaikekkan Journal of Medical Ultrasonics, vol. 31, No. 5, Sep. 15, 2004, pp. J347-J353 and p. J411.

(Continued)

*Primary Examiner* — Angela M Hoffa
*Assistant Examiner* — Vani Gupta
(74) *Attorney, Agent, or Firm* — Oblon, McClelland, Maier & Neustadt, L.L.P.

(57) ABSTRACT

The invention provides an ultrasonic diagnostic apparatus that scans an object to be examined into which contrast medium bubbles are injected with ultrasonic waves to acquire an ultrasonic image of the object. The ultrasonic diagnostic apparatus includes an image data generating unit that generates a plurality of image data indicating information on the shape of an object to be examined on the basis of echo signals returning from the object, a setting unit that sets an interesting area which is smaller than the entire image area to first image data, which is reference image data, among the plurality of image data, a vector generating unit that compares at least one second image data different from the first image data among the plurality of image data with data in the interesting area to generate a motion vector (Continued)

indicating the motion between the first image data and the at least one second image data, an image correcting unit that corrects the blur of the first image data and the at least one second image data on the basis of the motion vector, and an image generating unit that generates a display image on the basis of the plurality of corrected image data.

23 Claims, 13 Drawing Sheets

(51) Int. Cl.
  *G01S 7/52* (2006.01)
  *A61B 6/00* (2006.01)
(52) U.S. Cl.
  CPC ........ *A61B 8/5276* (2013.01); *G01S 7/52041* (2013.01); *G01S 7/52063* (2013.01); *G01S 7/52074* (2013.01); *A61B 6/463* (2013.01); *A61B 6/466* (2013.01); *A61B 8/00* (2013.01); *A61B 8/466* (2013.01); *G01S 7/52077* (2013.01)
(58) Field of Classification Search
  CPC ..... A61B 8/483; A61B 8/5238; A61B 8/5276; G01S 7/52041; G01S 7/52063; G01S 7/52074; G01S 7/52077
  USPC .......................................... 600/443, 407–480
  See application file for complete search history.

(56) References Cited

U.S. PATENT DOCUMENTS

| | | |
|---|---|---|
| 6,149,597 A | 11/2000 | Kamiyama |
| 6,162,174 A | 12/2000 | Friemel |
| 6,368,277 B1 * | 4/2002 | Mao et al. .................... 600/441 |
| 6,468,218 B1 * | 10/2002 | Chen ...................... A61B 6/469 128/916 |
| 6,485,423 B2 * | 11/2002 | Angelsen et al. ............ 600/458 |
| 7,986,813 B2 * | 7/2011 | Hamanaka .................... 382/106 |
| 2003/0016782 A1 * | 1/2003 | Kaufman ............... A61B 6/032 378/50 |
| 2003/0212327 A1 * | 11/2003 | Wang et al. .................. 600/437 |
| 2004/0044283 A1 * | 3/2004 | Yoneyama ............... A61B 8/14 600/437 |
| 2004/0057607 A1 | 3/2004 | Breeuwer et al. |
| 2004/0120559 A1 | 6/2004 | Hall |
| 2004/0210138 A1 * | 10/2004 | Murashita et al. ........... 600/443 |
| 2004/0215076 A1 | 10/2004 | Kamiyama |
| 2005/0033123 A1 | 2/2005 | Gardner et al. |
| 2005/0228276 A1 * | 10/2005 | He et al. ........................ 600/437 |
| 2006/0116582 A1 | 6/2006 | Yoshida et al. |
| 2006/0241431 A1 | 10/2006 | Kamiyama |
| 2007/0076975 A1 * | 4/2007 | Abe ....................... H04N 5/243 382/274 |

FOREIGN PATENT DOCUMENTS

| | | |
|---|---|---|
| JP | 6-43237 | 2/1994 |
| JP | 11-155858 | 6/1999 |
| JP | 2000-217815 | 8/2000 |
| JP | 2001-17434 | 1/2001 |
| JP | 2004-321688 | 11/2004 |
| JP | 2006-55642 | 3/2006 |

OTHER PUBLICATIONS

European Office Action dated Jul. 27, 2018 in European Patent Application No. 07706523.3, 8 pages.

* cited by examiner

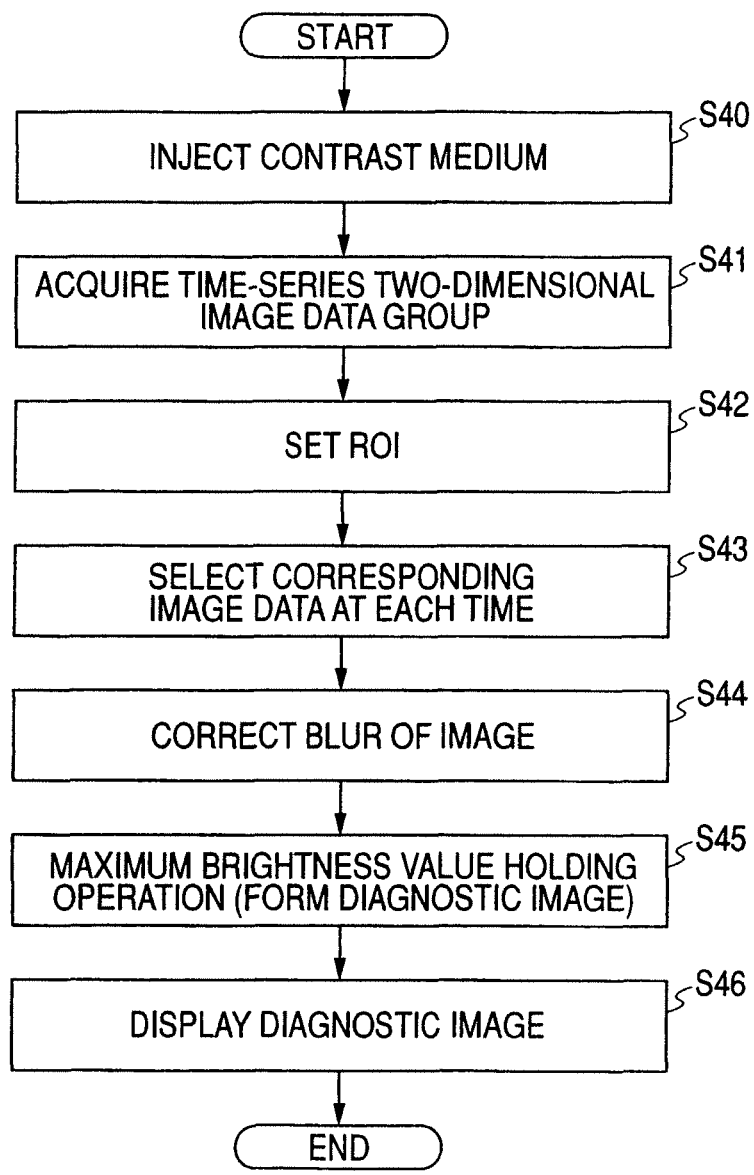

ULTRASONIC DIAGNOSTIC APPARATUS AND METHOD OF GENERATING ULTRASONIC IMAGE

CROSS REFERENCE TO RELATED APPLICATIONS

This is a Continuation Application of PCT Application No. PCT/JP2007/050176, filed Jan. 10, 2007, which was published under PCT Article 21(2) in Japanese.

This application is based upon and claims the benefit of priority from prior Japanese Patent Applications No. 2006-002661, filed Jan. 10, 2006; and No. 2006-140283, filed May 19, 2006, the entire contents of both of which are incorporated herein by reference.

BACKGROUND OF THE INVENTION

1. Field of the Invention

The present invention relates to an ultrasonic diagnostic apparatus and a method of generating an ultrasonic image capable of correcting the blur of an image due to the movement of an object to be examined or the movement of an operator's hand holding an ultrasonic probe.

2. Description of the Related Art

In recent years, a 'contrast echo method' of injecting an ultrasonic contrast medium into a vein has been used for ultrasonic diagnosis. The contrast echo method is a method of injecting the ultrasonic contrast medium into the vein, increasing a bloodstream signal, and evaluating the amount of the bloodstream in the heart or the liver. In many cases, minute bubbles of the contrast medium (contrast medium bubbles) serve as a reflective source. From the viewpoint of the property of bubbles, which is a delicate material, bubbles are broken by the mechanical operation of ultrasonic waves having a general diagnostic level, and as a result, the signal intensity from the scanning surface is lowered. Therefore, in order to observe the dynamic aspect of the reflux of the bloodstream in real time, a method of reducing the breaking of bubbles due to scanning, such as a method of forming an image by transmitting low sound pressure ultrasonic waves, is needed.

The following method has been developed considering the property of a material, such as the breaking of bubbles. That is, a low sound pressure ultrasonic wave is transmitted to observe the movement of bubbles filled in the scanning surface, a high sound pressure ultrasonic wave is transmitted to the scanning surface (strictly, in an object to be radiated) to break the bubble, and a low sound pressure ultrasonic wave is radiated to the scanning surface to observe the movement of bubbles flowing into the scanning surface. This method is called a 'replenishment method' (for example, see JP-A-11-155858).

The contrast medium bubbles are characterized in that it can form an image of a minute bloodstream which cannot be imaged by a color Doppler method. The imaging of the minute bloodstream is abnormal since few bubbles exist in the minute bloodstream. Therefore, a method of superposing the images of the contrast medium bubbles that appear to be abnormal to form a clear image of the structure of a minute blood vessel has been developed. This method is called a 'micro flow imaging (MFI) method' (for example, see JP-A-2004-321688).

In the MFI method, it is necessary to superpose ultrasonic images corresponding to a plurality of frames. Therefore, a person to be examined needs to hold his/her breath for a predetermined amount of time, or an operator needs to fix an ultrasonic probe for a predetermined amount of time.

However, it is difficult for the person to be examined to hold his/her breath for a predetermined amount of time, and it is not easy for an operator unaccustomed to the MFI method to fix the ultrasonic probe for a predetermined amount of time. Therefore, it is considerably effective to correct the blur of an ultrasonic image, in order to improve the quality of a displayed image in the MFI method.

A technique for correcting the blur of a continuous series of frames, such as moving pictures, has been used for video cameras on the market. A method of calculating relative motion vectors between frames of image data is used as a representative example. In this method, image data corresponding to one frame is divided into a plurality of areas, and the motion vector between the frames in each area is calculated on the basis of the correlation between the image data in the areas. When a plurality of motion vectors calculated for each area are used to correct the display position of the image data, it is possible to improve the visibility of a moving picture since the display position of an object does not vary even when a user's hand holding the camera is jiggled more or less.

A panoramic imaging technique, which is similar to a technique for correcting the blur of an ultrasonic diagnostic image, has been known. In this technique, ultrasonic images corresponding to a plurality of frames are acquired while moving an ultrasonic probe little by little, and overlapping portions of the ultrasonic images are combined with one another to form a wide still picture, such as a panoramic photograph. In the panoramic imaging technique, since it is necessary to combine overlapping portions of the ultrasonic images corresponding to a plurality of frames, relative motion vectors between frames are needed, similar to the ultrasonic images.

BRIEF SUMMARY OF THE INVENTION

However, it is relatively easy to correct the blur of a general tomographic image, that is, an ultrasonic image generated from an object to be examined not having a contrast medium injected thereinto. This is because tissue or skeleton, which serves as a mark when a motion vector is detected, is reflected to the general tomographic image.

However, since bubbles are abnormally dyed, a blur correcting technique used for a general ultrasonic image cannot be applied to angiography, that is, an ultrasonic image of an object to be examined having a contrast medium injected thereinto. In particular, in the MFI method, a high sound pressure ultrasonic wave is used to sweep away bubbles. Therefore, in order to form an image of replenishment, few marks for blur correction exist in the image generated immediately after the bubbles are swept away. Further, in the image generated immediately after the bubbles are swept away, the shapes of the imaged bubbles vary every moment, which makes is difficult to extract motion vectors.

Accordingly, it is an object of the present invention to provide an ultrasonic diagnostic apparatus and a method of generating an ultrasonic image capable of preventing a reduction in the quality of a diagnostic image even when an object to be examined or an ultrasonic probe moves more or less.

According to a first aspect of the present invention, there is provided an ultrasonic diagnostic apparatus that scans an object to be examined into which contrast medium bubbles are injected with ultrasonic waves to acquire an ultrasonic image of the object. The ultrasonic diagnostic apparatus includes: a transmitting/receiving unit that repeatedly transmits the ultrasonic waves to the object and acquires echo signals returning from the object; an image data generating unit that generates a plurality of image data indicating information on the shape of the object on the basis of the echo signals; a setting unit that sets an interesting area which is smaller than the entire image area to first image data, which is reference image data, among the plurality of image data; a vector generating unit that compares at least one second image data different from the first image data among the plurality of image data with data in the interesting area to generate a motion vector indicating the motion between the first image data and the at least one second image data; an image correcting unit that corrects the blur of the first image data and the at least one second image data on the basis of the motion vector; and an image generating unit that generates a display image on the basis of the plurality of corrected image data.

According to another aspect of the present invention, there is provided a method of generating an ultrasonic diagnostic image by scanning an object to be examined to which contrast medium bubbles are injected with ultrasonic waves. The method includes: repeatedly transmitting the ultrasonic waves to the object and generating a plurality of image data indicating information on the shape of the object on the basis of echo signals returning from the object; setting an interesting area which is smaller than the entire image area to first image data, which is reference image data, among the plurality of image data; comparing at least one second image data different from the first image data among the plurality of image data with data in the interesting area to generate a motion vector indicating the motion between the first image data and the at least one second image data; correcting the blur of the first image data and the at least one second image data on the basis of the motion vector; and generating a display image on the basis of the plurality of corrected image data.

BRIEF DESCRIPTION OF THE SEVERAL VIEWS OF THE DRAWING

FIG. 9 is a flow chart illustrating the flow of an MFI process including blur correction according to a fourth embodiment of the invention.

DETAILED DESCRIPTION OF THE INVENTION

Hereinafter, first to twelfth embodiment of the invention will be described with reference to the accompanying drawings.

First Embodiment

First, a first embodiment of the invention will be described with reference to FIGS. 1 to 6.

[Structure of Ultrasonic Diagnostic Apparatus]

Figure 1:
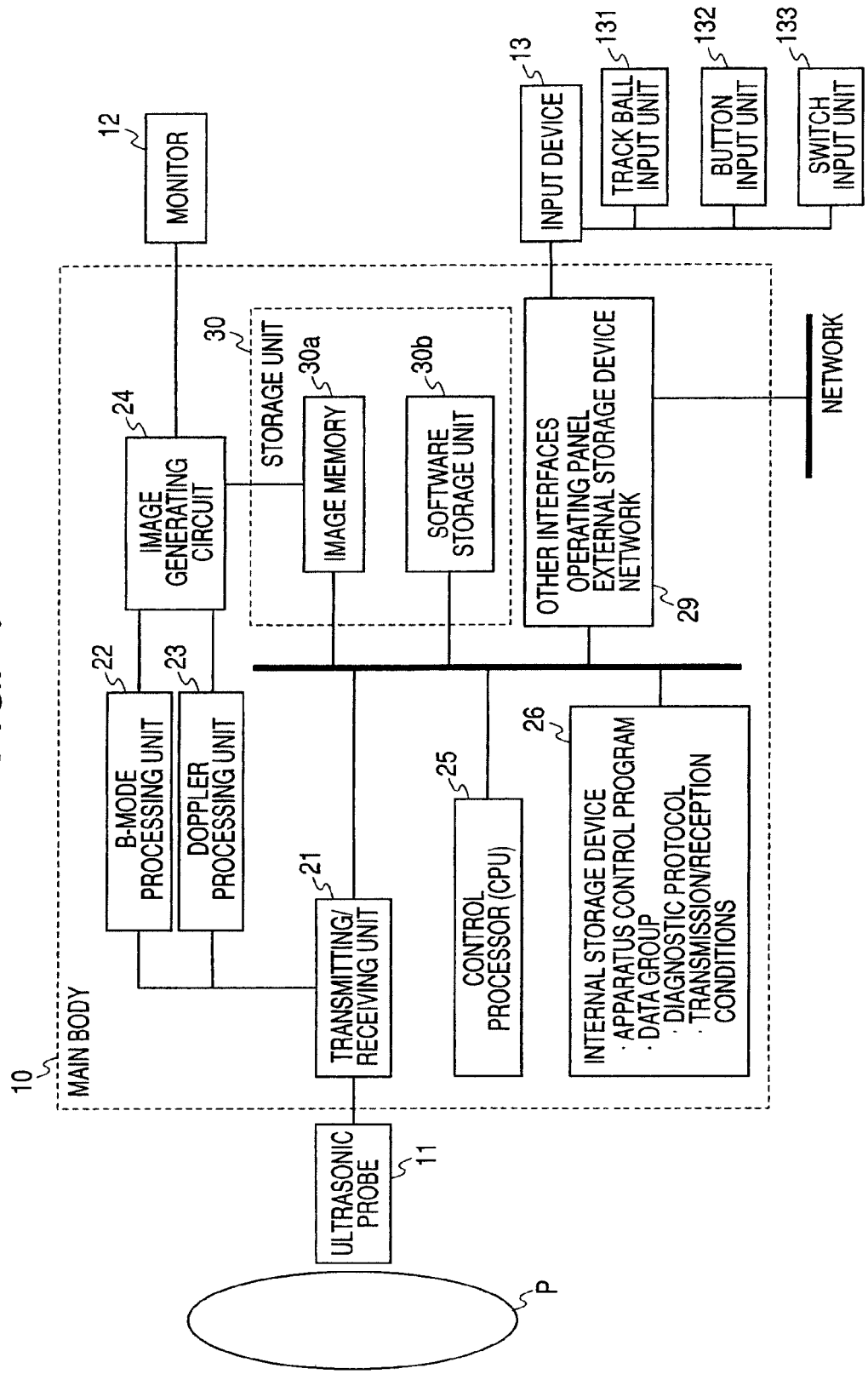
FIG. 1 is a block diagram illustrating an ultrasonic diagnostic apparatus according to a first embodiment of the invention.

FIG. 1 is a block diagram illustrating an ultrasonic diagnostic apparatus according to the first embodiment of the invention.

As shown in FIG. 1, the ultrasonic diagnostic apparatus according to the first embodiment includes a main body 10, an ultrasonic probe 11, a monitor 12, and an input device 13.

The main body 10 includes a transmitting/receiving unit 21, a B-mode processing unit 22, a Doppler processing unit 23, an image generating circuit 24, a control processor 25, an internal storage device 26, an interface 29, and a storage unit 30 having an image memory 30a and a software storage unit 30b.

For example, the transmitting/receiving unit 21 provided in the main body 10 is composed of hardware, such as an integrated circuit, or it may be a software program that is modularized in a software manner. Next, each component will be described below.

The ultrasonic probe 11 transmits or receives ultrasonic waves to or from a part of an object P to be examined, and is provided with a piezoelectric vibrator for transmitting/receiving ultrasonic waves. The piezoelectric vibrator is divided into a plurality of elements, and each of the elements forms a part of a so-called channel. When the ultrasonic probe 11 includes a 2D array vibrator, it can obtain three-dimensional data.

The ultrasonic waves (hereinafter, referred to 'transmission ultrasonic waves') transmitted from the ultrasonic probe 11 to the object P to be examined are sequentially reflected from the surfaces where acoustic impedance is discrete in the human body and are transmitted to the ultrasonic probe 11 as echo signals.

The amplitude of the echo signals depends on the difference in acoustic impedance between the discrete surfaces from which the ultrasonic waves are reflected. When the transmission ultrasonic wave is reflected from the surface of a movable object, such as bloodstream or a heart wall, a frequency shift occurs in the echo signal due to a speed component of the ultrasonic wave reflected from the movable object in the transmission direction by the Doppler effect.

The monitor 12 displays as a diagnostic display bloodstream information or morphological information in the object P to be examined on the basis of video signals transmitted from the image generating circuit 24. In addition, the monitor 12 displays an ROI mark on the diagnostic image.

The input device 13 is connected to the main body 10 and includes a track ball input unit 131, a button input unit 132, and a switch input unit 133 for inputting instructions of an operator to the main body 10.

Figure 2:
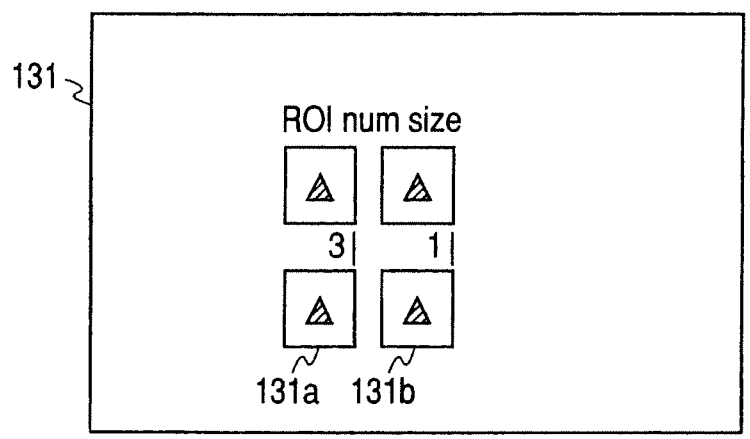
FIG. 2 is a diagram schematically illustrating various types of track balls according to the first embodiment of the invention.

FIG. 2 is a diagram schematically illustrating the track ball input unit 131 according to the first embodiment.

As shown in FIG. 2, the track ball input unit 131 includes a track ball 131a used for designating the number of ROIs and a track ball 131b used for designating the size of ROI.

Figure 3:
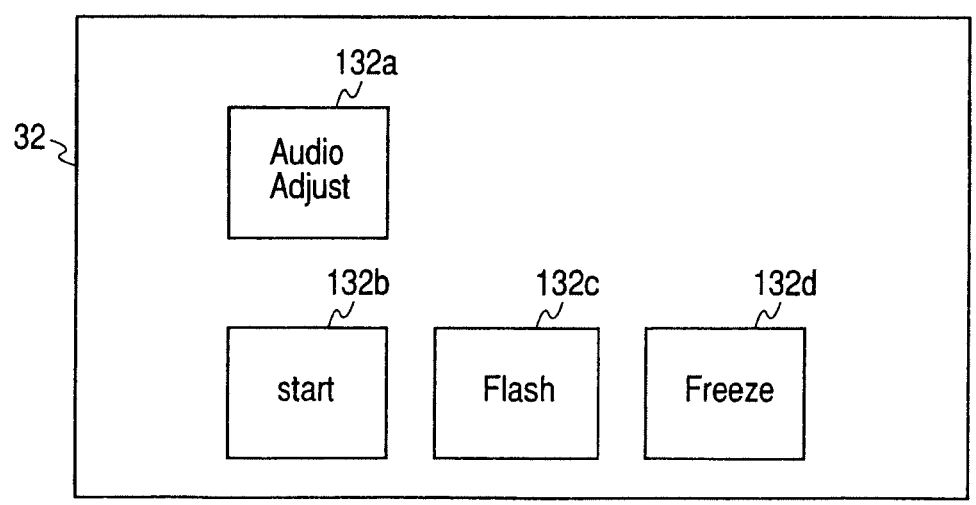
FIG. 3 is a diagram schematically illustrating various buttons according to the first embodiment of the invention.

FIG. 3 is a diagram schematically illustrating the button input unit 132 according to the first embodiment of the invention.

As shown in FIG. 3, the button input unit 132 includes an audio adjust button 132a used to instruct the start or end of the detection of movement, a start button 132b used to instruct to start or end the superposition of image data, and a flash button 132c used to instruct to perform high-sound pressure scanning, and a freeze button 132d used to instruct to stop the low-sound pressure scanning.

The instructions from the operator include an instruction to designate the shape of ROI, an instruction to designate the time when low-sound pressure scanning is performed, an instruction to designate the time when blur correction is performed, and an instruction to display or not display an ROI mark. The input device 13 further includes track balls, buttons, and switches corresponding to the instructions, in addition to the track balls 131a to 131b and the buttons 132a to 132c.

The transmitting/receiving unit 21 includes a pulse circuit, a delay circuit, and a trigger generating circuit. The pulse circuit repeatedly generates rate pulses for forming transmission ultrasonic waves at a predetermined rate frequency. The delay circuit gives a delay time required to condense a transmission ultrasonic wave for each channel and to determine transmission directivity to each of the rate pulses. The direction in which the ultrasonic waves from the ultrasonic probe 11 are transmitted is controlled by adjusting the delay time given by the delay circuit. The trigger generating circuit supplies a driving pulse to the ultrasonic probe 11 at a predetermined timing on the basis of the rate pulse whose delay time has been adjusted.

The transmitting/receiving unit 21 has a function of changing, for example, delay information, a transmission frequency, and a transmission driving voltage in an instant according to the instructions from the control processor 25. In particular, in order to change the transmission driving voltage, the transmitting/receiving unit 21 is formed of a linear-amplifier-type transmitting circuit capable of switching the value of the transmission driving voltage in an instant or a mechanism capable of electrically switching a plurality of power supply units.

Further, the transmitting/receiving unit 21 includes an amplifying circuit, an A/D converter, and an adder. The amplifier circuit amplifies the echo signal for each channel received by the ultrasonic probe 11. The A/D converter gives a delay time required to determine the reception directivity of ultrasonic waves to the echo signal amplified for every channel. The adder adds the delayed echo signals for each channel to generate a reception signal. In this way, a reflection component in a direction corresponding to the reception directivity of the echo signal is emphasized.

The B-mode processing unit 22 performs logarithmic amplification and an envelope curve detecting process on the reception signal output from the transmitting/receiving unit 21 to generate intensity data for representing the intensity of the reception signal as brightness.

The Doppler processing unit 23 obtains information on the speed of bloodstream, tissue, and bubbles of a contrast medium on the basis of the reception signal output from the transmitting/receiving unit 21 to generate blood stream data for average speed, dispersion, power, and a combination thereto.

The image generating circuit 24 converts the coordinates of the intensity data and the bloodstream data respectively output from the B-mode processing unit 22 and the Doppler processing unit 23 into scanning line signal strings of a video format that is representatively used for a television. In this way, a tomographic image related to the shape of the tissue of the object P to be examined, an image in which contrast medium bubbles flowing into a blood vessel are emphasized, an average speed image related to the speed of bloodstream, a dispersion image, a power image, and an image of a combination thereof are generated. The image generating circuit 24 includes a storage memory for storing image data. This structure makes it possible for an operator to view the image formed during examination after diagnosis.

The control processor (CPU) 25 serves as an information processing device and controls all components of the ultrasonic diagnostic apparatus. The control processor 25 reads out a control program for generating images and displaying the images from the internal storage device 26 and expands the read control program in the software storage unit 30b, thereby controlling various processes.

The control processor 25 creates a search area on the image data and detects the brightness of pixels included in the search area. In addition, the control processor 25 generates motion vectors for realizing the motion between image data on the basis of the brightness of a plurality of pixels included in ROI of a plurality of image data.

The internal storage device 26 stores control programs for generating images and displaying the images, diagnostic information (ID, for example, doctor's observations and diagnosis), a diagnostic protocol, transmitting/receiving conditions, and data groups. In particular, the internal storage device 26 stores control programs for executing, for example, a scanning sequence for transmitting/receiving ultrasonic waves, setting of ROI, blur correction, a differential image generating process, a brightness value holding process, and a superposition display process. In addition, the internal storage device 26 is used to store the image data in the image memory 30a, if necessary. Further, data stored in the internal storage device 26 may be transmitted to an external peripheral apparatus through the interface 29.

The interface 29 is an interface for the input device 13, a network, and an additional external storage device. Data for an obtained ultrasonic image or the analysis result thereof may be transmitted to another apparatus through the interface 29 over the network.

The image memory 30a is a storage memory for storing image data output from the image data generating circuit 24. An operator can call the image data stored in the storage memory after diagnosis, and the image data is displayed as a still picture or a moving picture composed of a plurality of frames. The image memory 30a stores output signals of the transmitting/receiving unit 21 (referred to as radio frequency signals), brightness signals having passed through the transmitting/receiving unit 21, and other raw data, and image data acquired over the network, as occasion demands.

[Usage of Ultrasonic Diagnostic Apparatus]

First, the operator operates the track ball 131a and the track ball 131b to designate the number of ROIs and the size of ROI, respectively. In this embodiment, the shape of ROI is previously set to a rectangular shape, and is designated by operating, for example, the track balls.

Next, low sound pressure scanning starts. The low sound pressure scanning is performed to display the reflux of bloodstream as an image, and is performed several times. The low sound pressure scanning may start before the number of ROIs and the size thereof are set.

Ultrasonic waves used for the low sound pressure scanning are set to a sufficiently low sound pressure not to break the contrast medium bubbles. Therefore, whenever the low sound pressure scanning is performed, image data corresponding to one frame of images of the contrast medium bubbles is generated. The generated image data is stored in the image memory 30a and simultaneously displayed on the monitor 12.

When the start button 132b is turned on during the low sound pressure scanning, image data generated in the next stage are superposed to generate superposed image data. A maximum brightness value holding operation is used to superpose image data. The maximum brightness value holding operation is a method of using pixels having the highest brightness among a plurality of pixels spatially corresponding to each other to form an image on the basis of image data corresponding to a plurality of frames. Therefore, when the maximum brightness value holding operation is performed, images of the contrast medium bubbles extracted from the image data are connected to each other, and as a result, the structure of a blood vessel of the object P to be examined is extracted from the superposed image data. The superposed image data is displayed on the monitor 12 as a diagnostic image. That is, when the start button 132b is turned on during the low sound pressure scanning, MFI starts.

When the start button 132b is turned off during the superposition of image data, the superposition of image data performed up to now stops, and the image data generated whenever the low sound pressure scanning is performed is displayed on the monitor 12.

When the flash button 132c is turned on during the low sound pressure scanning, high sound pressure scanning corresponding to one frame is performed. The high sound pressure scanning is called 'flash'.

The ultrasonic waves used for the high sound pressure scanning are set to a sufficiently high sound pressure level to break a contrast medium bubble. Therefore, when the high sound pressure scanning is performed, all contrast medium bubbles existing on the scanning surface are broken, which causes the image of the contrast medium bubbles to disappear from the diagnostic image displayed on the monitor 12. As a result, a dark image is displayed on the monitor 12. However, the dark image does not last for a long time. When a certain amount of time has elapsed, the image of a thick blood vessel formed by the contrast medium bubbles appears gradually.

When the freeze button 132d is turned on during the low sound pressure scanning, the low sound pressure scanning stops. In this case, when the superposition of image data is performed or when the movement detecting mode is executed, these operations also stop.

When the audio adjust button 132a is turned on during the low sound pressure scanning, the movement detecting mode starts. The movement detecting mode is a standby mode in movement detection, but no process is actually performed in the movement detecting mode.

Next, the movement detecting mode will be described below.

Figure 4:
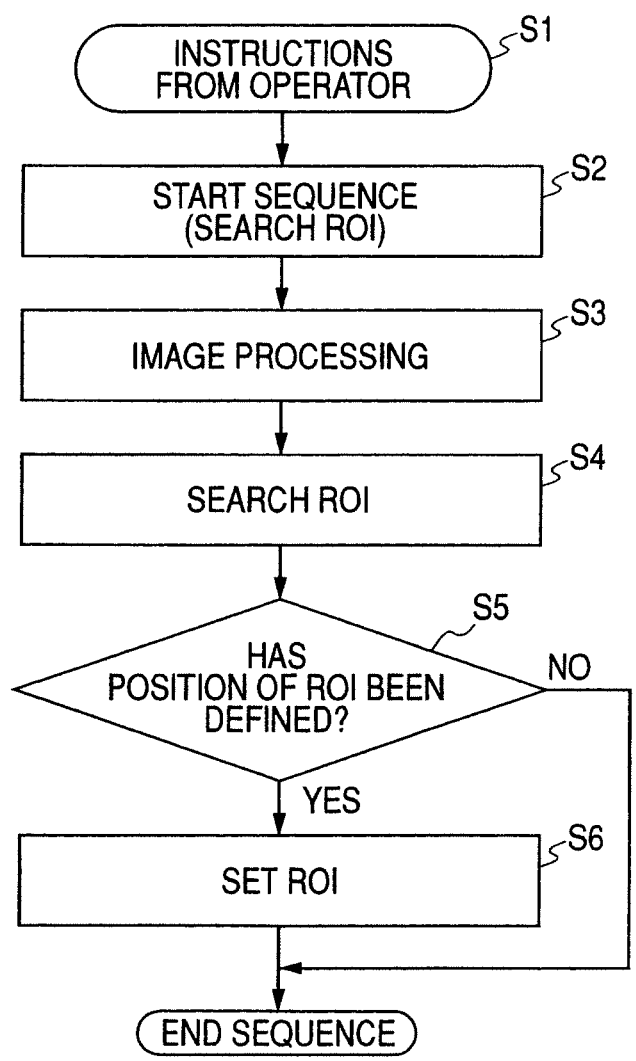
FIG. 4 is a flow chart illustrating a process performed by the ultrasonic diagnostic apparatus according to the first embodiment of the invention.

FIG. 4 is a flow chart illustrating a sequence of setting ROI according to this embodiment.

As shown in FIG. 4, when the start button 132b is turned on in the movement detecting mode (step S1), a sequence of setting ROI starts (step S2), and image data immediately after that time is designated to standard image data.

When the standard image data is designated, various types of image processing are performed on the standard image data to generate reference image data actually used as a search target of ROI (step S3). For example, an average value process or a threshold value process is performed on the standard image data as image processing.

When the average value process is used, image data for several frames that are generated immediately before the standard image data is used to generate the reference image data on the basis of the average brightness of a plurality of pixels spatially corresponding to each other in the image data.

When the threshold value process is used, the average brightness of all frames of the standard image data or brightness higher than the average brightness is set to a threshold value, and the reference image data is generated on the basis of the brightness of pixels of the standard image data binarized by the threshold value.

Therefore, little noise exists in the reference image data generated by the average value process or the threshold value process, but only the image of the contrast medium bubble or only the tissue of a living body is reflected to the reference image data.

When the reference image data is generated, a search area having the same size and shape as ROI is generated on the reference image data. The search area moves across all entire reference image data. Whenever the search image area moves by one pixel, the brightness of the pixel included therein is detected (step S4).

Whenever image areas (hereinafter, referred to as 'image areas satisfying conditions of ROI') in which the number of pixels having brightness higher than a threshold value K is larger than a threshold value M are detected, one of the image areas having the largest number of pixels having brightness higher than the threshold value K is searched (Yes in step S5), and ROI is set to the image area (step S6). In this way, the sequence of setting ROI is completed (step S7).

Figure 5:
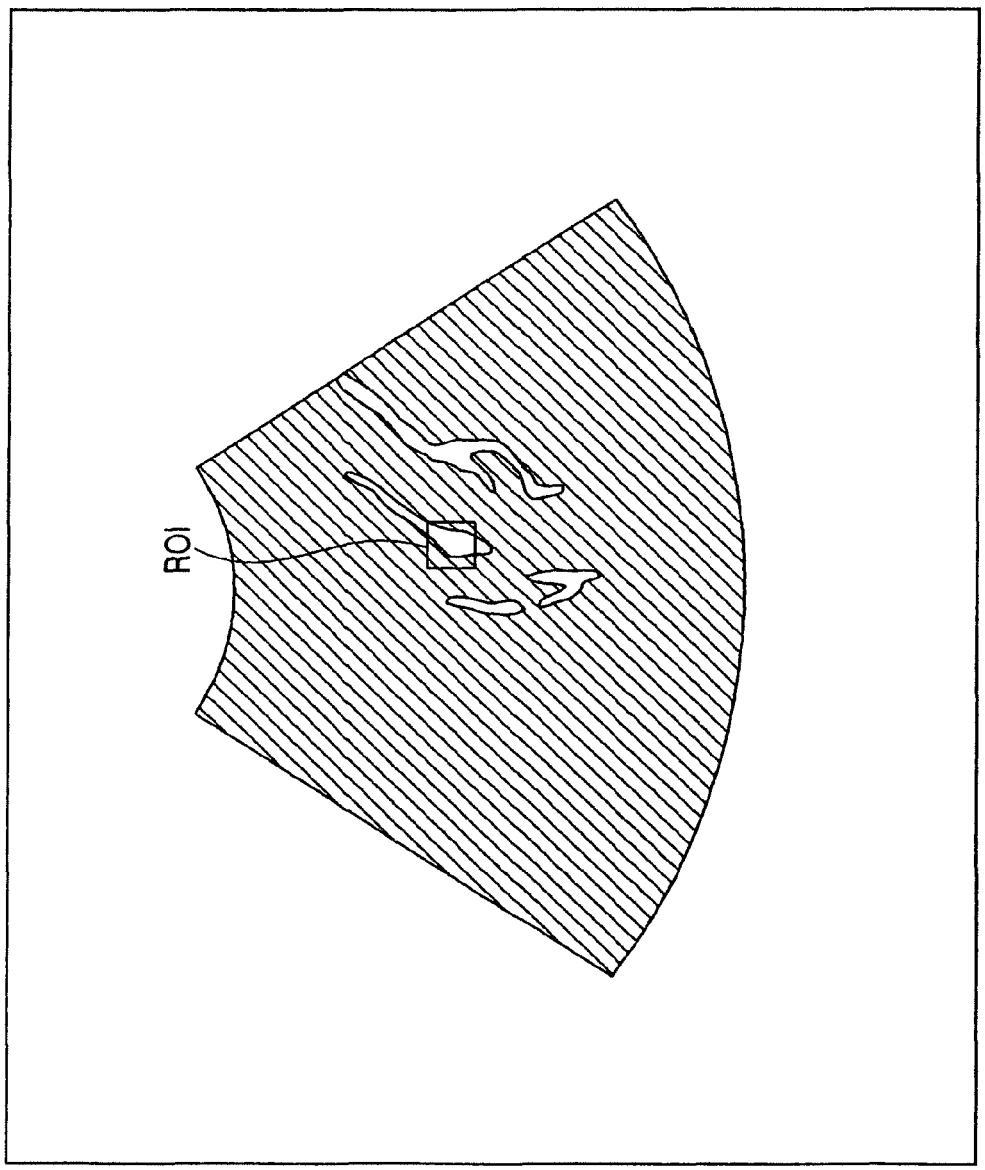
FIG. 5 is a diagram schematically illustrating a diagnostic image having an ROI mark superposed thereon according to the first embodiment of the invention.

As shown in FIG. 5, the set ROI is superposed on the diagnostic image displayed on the monitor 12 as a rectangular-frame-shaped ROI mark. When a plurality of ROIs are used, the sequence of setting ROI is repeatedly performed by a number of times corresponding to the number of ROIs used. Immediately after a contrast medium is injected into an object to be examined or flash transmission is performed, a high-brightness area (that is, an area having the contrast medium injected thereinto) is not displayed on a screen. Therefore, in general, the high-brightness area appears gradually on the screen. When one high-brightness area appears on the image, one ROI is set according to the sequence of setting ROI, and when two high-brightness areas appear on the image, two ROIs are set. In this way, the number of ROIs set increases with an increase in the number of high-brightness areas on the image. For example, when three ROIs are used, three high-brightness areas satisfying conditions of ROI appear on the image. In this embodiment, the sequence of setting ROI is repeatedly performed until three ROIs corresponding to the three high-brightness areas are set.

If no image area satisfying the conditions of ROI appears on the image even when the search area moves across all the reference image data (No in step S5), the sequence of setting ROI ends (step S7).

When the image area satisfying the conditions of ROI does not appear and thus the sequence of setting ROI ends, image data subsequently generated is designated to the standard image data, and a sequence of searching ROI is performed again. In this way, the sequence of setting ROI is repeated until ROI is set.

Then, an area (a corresponding area) corresponding to ROI is set on each image data subsequent to the standard image data on the basis of the ROI on the standard image data (reference image data). The setting of the corresponding area makes it possible to sweep an area having the same shape and size as ROI on the next image data and to set an area having a brightness distribution pattern closest to that of ROI as the corresponding area.

When ROI is set to each image data according to the above-mentioned procedure, motion vectors representing the movement of the standard image data and the image data subsequent to the standard image data are generated from the correlation between the brightness of pixels included in ROI of the standard image data and the brightness of pixels included in the corresponding area of each image data subsequent to the standard image data. However, a method of generating the motion vectors is not limited thereto. For example, SAD (sum of absolute difference), which is a block matching method generally used to recognize movement, may be used as the method of generating the motion vectors.

When the motion vectors are generated, the display position of the image data subsequent to the standard image data is corrected on the basis of the motion vectors. In this way, corrected image data having little motion blur with respect to the standard image data is generated.

Whenever the corrected image data is generated, the corrected image data is superposed on the standard image data by the maximum brightness value holding operation. In the period in which the corrected image data is superposed, images of contrast medium bubbles flowing into the scanning surface are connected to each other, and the structure of blood vessels of the object P to be examined is extracted to the diagnostic image displayed on the monitor 12. In addition, the blur of the corrected image data superposed on the standard image data is corrected by a pre-process, which causes a very clear diagnostic image to be displayed on the monitor 12 even when corrected image data corresponding to a plurality of frames is superposed. Therefore, it is possible to obtain a very clear diagnostic image without being affected by the movement of the object P to be examined or the jiggling of a hand holding the ultrasonic probe 11.

When there is no area satisfying the conditions of ROI in image data for first and second frames, image data for a third frame is designated as the standard image data. The image data for the first and second frames are superposed on the image data for the third frame, which is the standard image data, similar to corrected image data generated on the basis of image data for frames next a fourth frame.

The blur of the image data for the first and second frames is not corrected, but the image data for the first and second frames are so dark that an area satisfying the conditions of ROI does not appear. Therefore, even when these image data are superposed on the standard image data, the quality of a diagnostic image is not affected at all.

Next, blur correction immediately after flash will be described below.

When the start button 132b is turned on immediately after flash, almost dark image data is designated as the standard image data. However, in this embodiment, ROI is set to an area having relatively high brightness in the dark image data immediately after flash on the basis of the brightness of pixels included in the reference image data. Therefore, it is easy to obtain the correlation between the brightness of pixels in ROI of the reference image data and the brightness of pixels in ROI of image data subsequent to the standard image data, and the blur of the image data subsequent to the standard image data is accurately corrected. Thus, a very clear diagnostic image is displayed on the monitor 12.

Next, ROI and a diagnostic image after flash will be described below.

FIGS. 6A to 6E are diagrams schematically illustrating diagnostic images corresponding to five frames that are generated after flash according to this embodiment. In FIGS. 6A to 6E, a white portion indicates a bright area, and a hatched portion indicates a dark area.

Figure 6A:
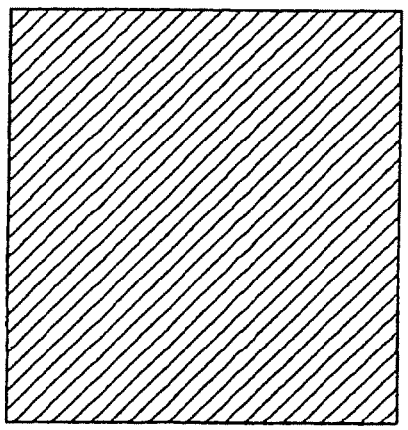
FIG. 6A is a diagram schematically illustrating five frames of diagnostic images generated after flash according to the first embodiment of the invention.
Figure 6B:
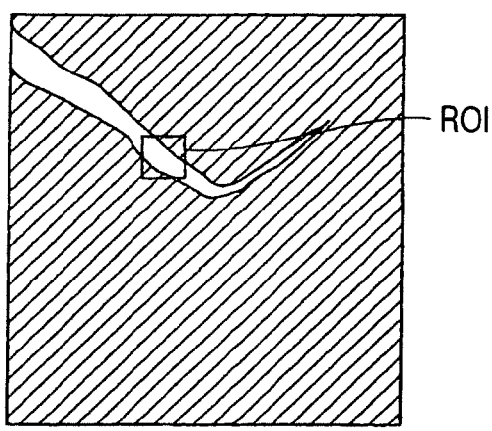
FIG. 6B is a diagram schematically illustrating five frames of diagnostic images generated after flash according to the first embodiment of the invention.
Figure 6C:
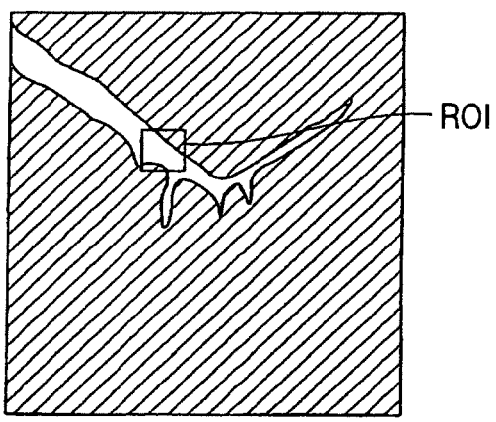
FIG. 6C is a diagram schematically illustrating five frames of diagnostic images generated after flash according to the first embodiment of the invention.
Figure 6D:
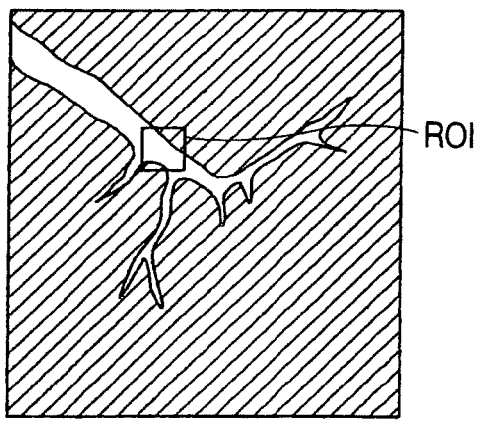
FIG. 6D is a diagram schematically illustrating five frames of diagnostic images generated after flash according to the first embodiment of the invention.
Figure 6E:
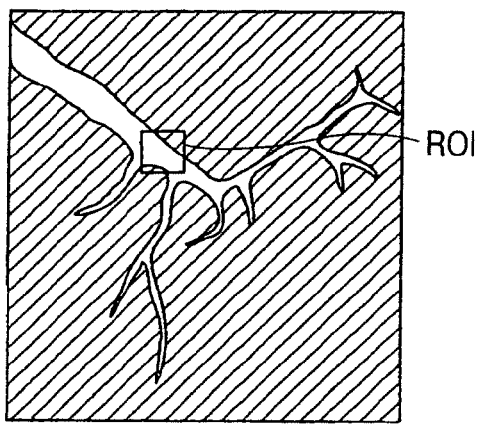
FIG. 6E is a diagram schematically illustrating five frames of diagnostic images generated after flash according to the first embodiment of the invention.

FIG. 6A is a diagram illustrating a diagnostic image at the time of flash, FIG. 6B is a diagram illustrating a diagnostic image corresponding to a first frame after flash, FIG. 6C is a diagram illustrating a diagnostic image corresponding to a second frame after flash, FIG. 6D is a diagram illustrating a diagnostic image corresponding to a third frame after flash, and FIG. 6E is a diagram illustrating a diagnostic image corresponding to a fourth frame after flash.

That is, the diagnostic image corresponding to the first frame is image data corresponding to the first frame that is generated at the beginning after flash. The diagnostic image corresponding to the second frame is the superposition of image data corresponding to the first and second frames. The diagnostic image corresponding to the third frame is the superposition of image data corresponding to the first to third frames. The diagnostic image corresponding to the fourth frame is the superposition of image data corresponding to the first to fourth frames. The diagnostic image corresponding to the fifth frame is the superposition of image data corresponding to the first to fifth frames.

As shown in FIG. 6A, when flash is performed, a dark diagnostic image is displayed on the monitor 12 once. When a predetermined time elapsed after the flash is performed, contrast medium bubbles flow from a thick blood vessels existing on the scanning surface, and the structure of the blood vessel of the object P to be examined is gradually extracted to the diagnostic image. In this case, when the sequence of setting ROI starts, ROI is set to an area satisfying conditions, as shown in FIG. 6B. When a predetermined time elapsed after ROI is set, the structure of the blood vessel becomes clearer, as shown in FIGS. 6C to 6E. In this case, the position of ROI set at the beginning does not vary.

In this embodiment, in the search of ROI, the brightness of pixels included in the search area is binarized by the threshold value K. However, the invention is not limited thereto. For example, a histogram for the brightness of pixels included in the search area may be made, and the search of ROI may be performed on the basis of the brightness of the top predetermined percent (for example 20%) of pixels included in the search area. In this case, noise components have little effect on the search of ROI, which makes it unnecessary to perform image processing, such as the average value process or the threshold value process.

Alternatively, two threshold values may be provided, and the search of ROI may be performed on the basis of a pixel having a brightness value between the two threshold values. In general, when contrast medium bubbles flow into a thick blood vessel, the brightness of the blood vessel excessively increases. However, in some cases, the thick blood vessel may not sufficiently serve as a characteristic area for correcting blur due to the thickness of the blood vessel, even when ROI is set to the area including the thick blood vessel. Therefore, the pixel having excessively high brightness is excluded from the object of ROI search, which makes it possible to extract a characteristic area suitable for correcting blur as ROI.

(Effects of First Embodiment)

In this embodiment, the image data immediately after the start button 132b is turned on is designated to the standard image data. Then, ROI is set to an area including a thick blood vessel in which the images of contrast medium bubbles are clustered close together on the basis of the brightness of reference image data generated from the standard image data.

Therefore, it is easy to obtain the correlation between the brightness of pixels in ROI of the reference image data and the brightness of pixels in a corresponding area of each image data subsequent to the standard image data, and the blur of the image data subsequent to the standard image data is accurately corrected. As a result, a very clear diagnostic image is generated by superposition.

In this embodiment, the image data immediately after the flash button 132c is pushed is designated to the standard image data. Then, ROI is set to an area including a thick blood vessel in which the images of contrast medium bubbles are rapidly restored on the basis of the brightness of reference image data generated from the standard image data.

In this way, even when few areas, serving as marks for correcting blur, exist in the reference image data, such as immediately after flash, ROI is automatically set to an area including a thick blood vessel in which contrast medium bubbles dye at relatively high speed.

Therefore, it is easy to obtain the correlation between the brightness of pixels in ROI of the reference image data and the brightness of pixels in a corresponding area of each image data subsequent to the standard image data, and the blur of the image data subsequent to the standard image data is accurately corrected. As a result, a very clear diagnostic image is generated by superposition.

In this embodiment, noise components are previously removed from the reference image data by image processing. Therefore, noise has no effect on the setting of ROI, which makes it possible to accurately set ROI in an area including a thick blood vessel.

In this embodiment, the number of pixels included in ROI is smaller than the number of pixels in all image data. Therefore, it is possible to reduce the amount of calculation required to calculate the correlation between the brightness of pixels in ROI of the reference image data generated from the standard image data and the brightness of pixels in a corresponding area of each image data subsequent to the standard image data.

In this embodiment, when the flash button 132c is turned on, blur correction starts instantaneously. Then, the images of contrast medium bubbles flowing into the scanning surface immediately after flash are superposed without omission. As a result, the structure of blood vessels of the object P to be examined is accurately extracted to a diagnostic image.

In this embodiment, an ROI mark is superposed on a diagnostic image displayed on the monitor 12. Therefore, the operator can check whether ROI is accurately set while viewing the diagnostic image displayed on the monitor 12.

In this embodiment, the input device 13 includes a button or a switch for switching the display and non-display of the ROI mark. Therefore, when diagnosis is interrupted by the ROI mark, the operator can simply remove the ROI mark.

In this embodiment, the input device 13 includes a button for designating the time when blur correction starts, that is, the start button 132b, and the flash button 132c. Therefore, the operator can start blur correction at a desired timing, which makes it possible to obtain a diagnostic image very suitable for the symptoms or conditions of the object P to be examined.

In this embodiment, the input device 13 includes the track ball for designating the time when blur correction is performed. Therefore, the operator can repeatedly check a variation in the reflux of the bloodstream until a predetermined time elapses after the start of the blur correction.

Further, in this embodiment, MFI has been described above, but the invention is not limited thereto. That is, the invention can be applied to 'Panoramic imaging' described in 'Background Art' as long as a plurality of image data can be superposed.

In this embodiment, the number of ROIs and the sizes thereof are input by the input device 13, but the invention is not limited thereto. For example, the number of ROIs and the sizes thereof may be automatically set on the basis of the brightness of pixels included in the reference image data.

(First Modification of First Embodiment)

MFI may be executed on the basis of a plurality of image data that have been acquired by the low sound pressure scanning and stored in the image memory 30a. In this case, the blur of image data is also corrected prior to the standard image data, and the corrected image data is also superposed on the standard image data. That is, the corrected image data generated on the basis of the image data prior to the standard image data may be superposed on the standard image data. When the blur of image data prior to the standard image data is corrected, the influence of the deflection between frames is reduced, which makes it possible to improve the quality of a diagnostic image.

(Second Modification of First Embodiment)

A common ROI that can be used to correct the blur of a plurality of image data acquired by the low sound pressure scanning is set on the basis of the brightness of the plurality of image data. This is effective in executing MFI on the basis of a plurality of image data that have been acquired by the low sound pressure scanning and stored in the image memory 30a.

(Third Modification of First Embodiment)

Next, a third modification of this embodiment will be simply described with reference to FIG. 7.

Figure 7:
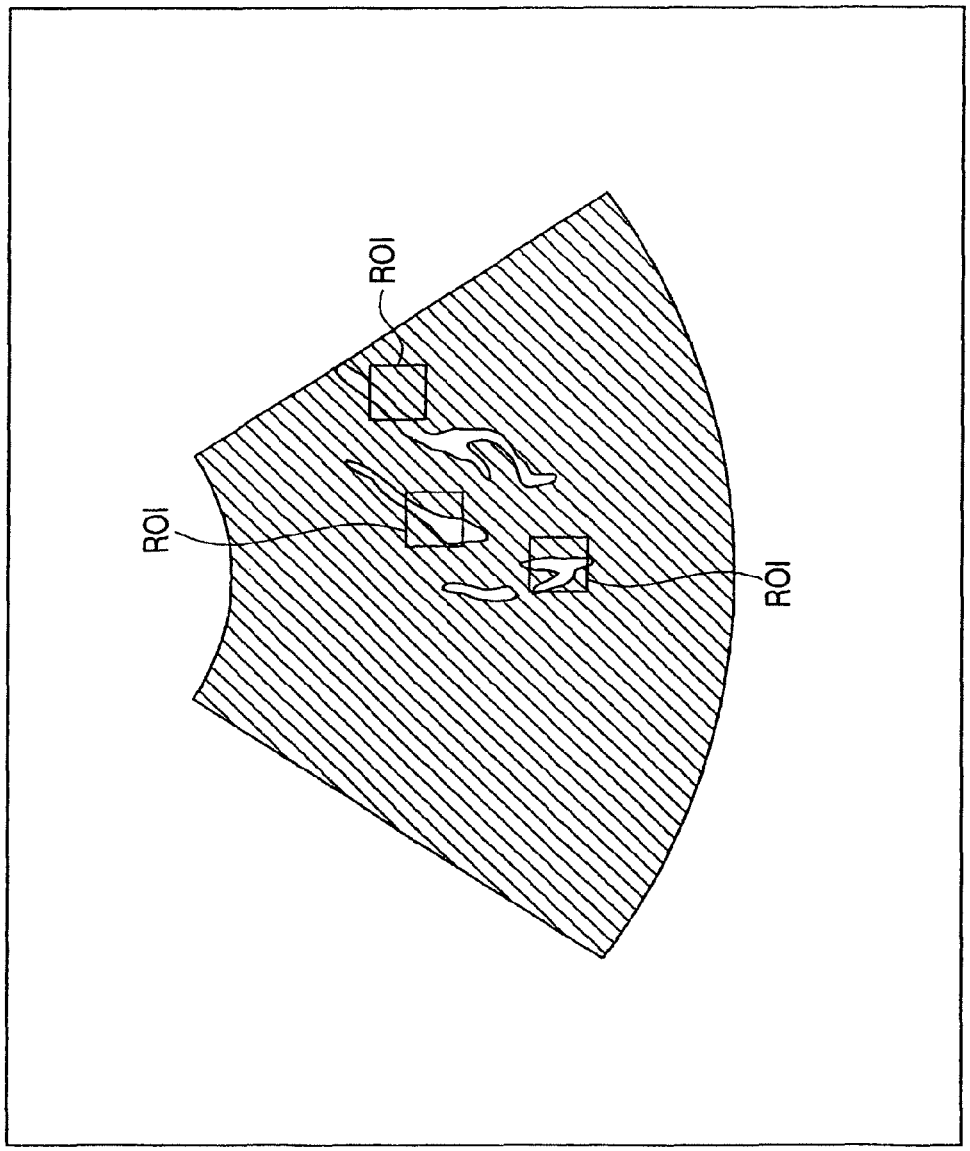
FIG. 7 is a diagram schematically illustrating a diagnostic image having an ROI mark superposed thereon according to a modification of the first embodiment of the invention.

FIG. 7 is a diagram schematically illustrating a diagnostic image having three ROI marks superposed thereon according to the third modification.

As shown in FIG. 7, the three ROI marks make it possible to correct the rotational deviation among frames of image data. Even when the three ROI marks are combined, the number of pixels included in the ROI marks is considerably smaller than the number of pixels of all image data, which makes it possible to considerably reduce the amount of calculation, as compared to a conventional technique for generating motion vectors using pixels of all image data.

(Fourth Modification of First Embodiment)

This embodiment may be effective in performing the maximum brightness value holding operation using three-dimensional image data (that is, between time-series volume data, the values of voxels whose spatial positions correspond to one another are traced over time, and a voxel having the largest value is used to form an image). In this case, a search area, an image area satisfying ROI conditions, and a set ROI are all three-dimensional areas, and the values of voxels included in each area are used to execute the above-mentioned algorithm, thereby correcting the blur among volume data.

(Fifth Modification of First Embodiment)

The diagnostic image generated by MFI using the blur correction according to this embodiment and the diagnostic image generated by MFI not using the blur correction according to this embodiment may be displayed at the same time (for example, the diagnostic images may be superposed side by side or the diagnostic images having different colors may be superposed). Alternatively, the diagnostic image using the blur correction and the diagnostic image not using the blur correction may be selectively displayed. In this way, it is possible to provide wide diagnostic information and realize a diagnostic image having a higher degree of freedom than that of the related art.

(Sixth Modification of First Embodiment)

In the blur correction according to this embodiment, when ROI is set in a bloodstream area of a thick blood vessel, the set ROI becomes a high-brightness area. Therefore, in this case, it is difficult to specify a corresponding area on each image data subsequent to the standard image data and to calculate the motion vectors.

In order to solve these problems, in the blur correction, ROI including a high-brightness area in which contrast medium bubbles are dyed (for example, an area having brightness equal to or higher than a first threshold value) and a low-brightness area not related to the contrast medium bubbles (for example, an area having brightness equal to or smaller than a second threshold value) may be used on the standard image data (reference image data). This structure prevents a brightness distribution pattern of ROI from having high brightness. Therefore, it is possible to appropriately specify an area corresponding to ROI on the frame subsequent to the standard image data and thus to perform appropriate blur correction.

Second Embodiment

Next, a second embodiment of the invention will be described below with reference to the drawings.

In the second embodiment, even if ROI is set once, the setting of ROI is performed whenever image data is generated. That is, when new image data is generated even if ROI has been set already, image data immediately before that time is designated to the standard image data. Then, reference image data is generated from the newly designated standard image data, and ROI is set on the basis of the reference image data.

However, a sequence of setting ROI is performed only when ROI is set first. When ROI is set two or more times, ROI is reset on the basis of ROI used to correct the blur of the image data immediately before the latest stage and a resultant vector of all motion vectors having already been generated. The motion vector means a vector representing the motion of a continuous series of image data.

That is, ROI used to correct the blur of image data corresponding to an n-th frame is set on the basis of ROI used to correct the blur of image data corresponding to an (n−1)-th frame and a resultant vector of all motion vectors generated until the blur of the image data corresponding to an (n−1)-th frame is corrected.

Third Embodiment

Next, a third embodiment of the invention will be described with reference to FIG. 8.

In the third embodiment, whenever image data is generated, a sequence of setting ROI is executed to set ROI on the basis of the brightness of each image data. However, in the second embodiment, the sequence of setting ROI is set only when ROI is set first. Therefore, once ROI is set, the next ROI is set on the basis of the set ROI and a motion vector. The third embodiment is different from the second embodiment on the above-mentioned point.

FIGS. 8A to 8E are diagram schematically illustrating diagnostic images corresponding to five frames generated after flash according to the third embodiment of the invention. In FIGS. 8A to 8E, a white portion indicates a bright area, and a hatched portion indicates a dark area.

Figure 8A:
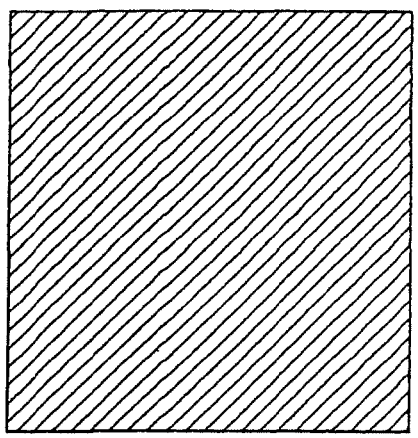
FIG. 8A is a diagram schematically illustrating five frames of diagnostic images generated after flash according to a third embodiment of the invention.
Figure 8B:
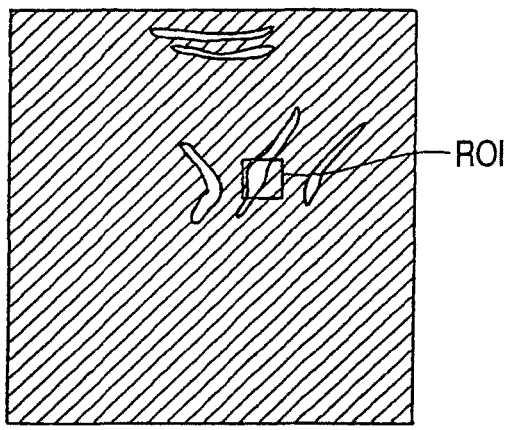
FIG. 8B is a diagram schematically illustrating five frames of diagnostic images generated after flash according to the third embodiment of the invention.
Figure 8C:
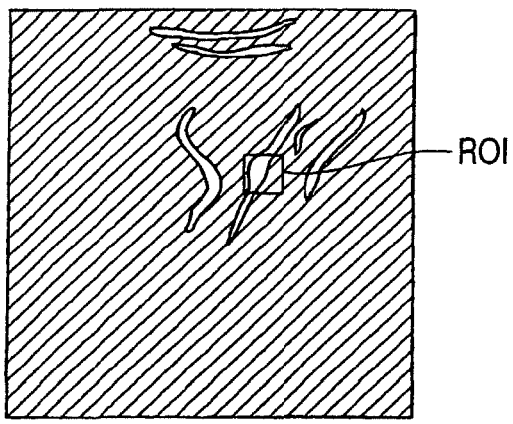
FIG. 8C is a diagram schematically illustrating five frames of diagnostic images generated after flash according to the third embodiment of the invention.
Figure 8D:
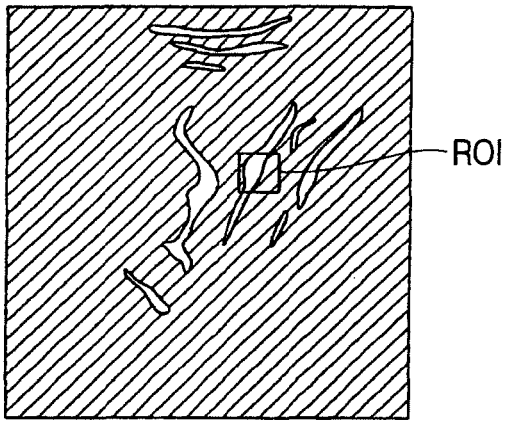
FIG. 8D is a diagram schematically illustrating five frames of diagnostic images generated after flash according to the third embodiment of the invention.
Figure 8E:
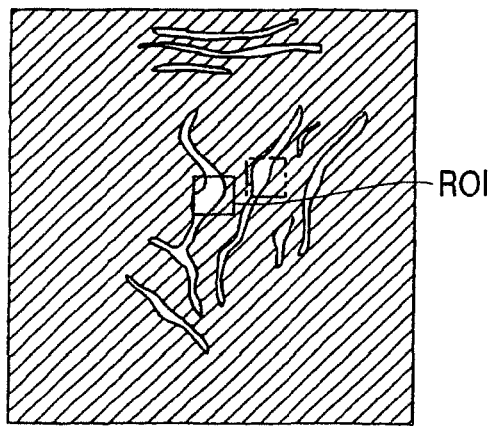
FIG. 8E is a diagram schematically illustrating five frames of diagnostic images generated after flash according to the third embodiment of the invention.

FIG. 8A is a diagram illustrating a diagnostic image at the time of flash, FIG. 8B is a diagram illustrating a diagnostic image corresponding to a first frame after flash, FIG. 8C is a diagram illustrating a diagnostic image corresponding to a second frame after flash, FIG. 8D is a diagram illustrating a diagnostic image corresponding to a third frame after flash, and FIG. 8E is a diagram illustrating a diagnostic image corresponding to a fourth frame after flash.

That is, the diagnostic image corresponding to the first frame is image data corresponding to the first frame that is generated at the beginning after flash. The diagnostic image corresponding to the second frame is the superposition of image data corresponding to the first and second frames. The diagnostic image corresponding to the third frame is the superposition of image data corresponding to the first to third frames. The diagnostic image corresponding to the fourth frame is the superposition of image data corresponding to the first to fourth frames. The diagnostic image corresponding to the fifth frame is the superposition of image data corresponding to the first to fifth frames.

As shown in FIGS. 8B to 8D, in the diagnostic images corresponding to the second to fourth frames, ROIs are set at the same position. This is because the sequence of setting ROI is performed on the third and fourth frames of the image data and ROI better than the existing ROI is not detected. However, as shown in FIG. 8E, in the diagnostic image according to the fifth frame, a new ROI is set. The new ROI is represented by a solid line, and a removed ROI mark is represented by a dotted line. The position of ROI moves because, when ROI is searched on the basis of the image data corresponding to the fifth frame, ROI better than the existing ROI is detected.

When the sequence of setting ROI is performed whenever image data is generated, it is possible to stably obtain a high-quality diagnostic image while accurately correcting the movement of the image data.

Further, the ultrasonic probe 11 moves in the direction in which a lens is disposed. Therefore, even when a blood vessel, which is a mark for blur correction until that time, (actually, the image of contrast medium bubbles) is removed from the scanning surface, it is possible to accurately correct the movement of the ultrasonic probe 11 in the lens direction since a new optimum ROI is set at a movement destination.

Fourth Embodiment

Figure 10:
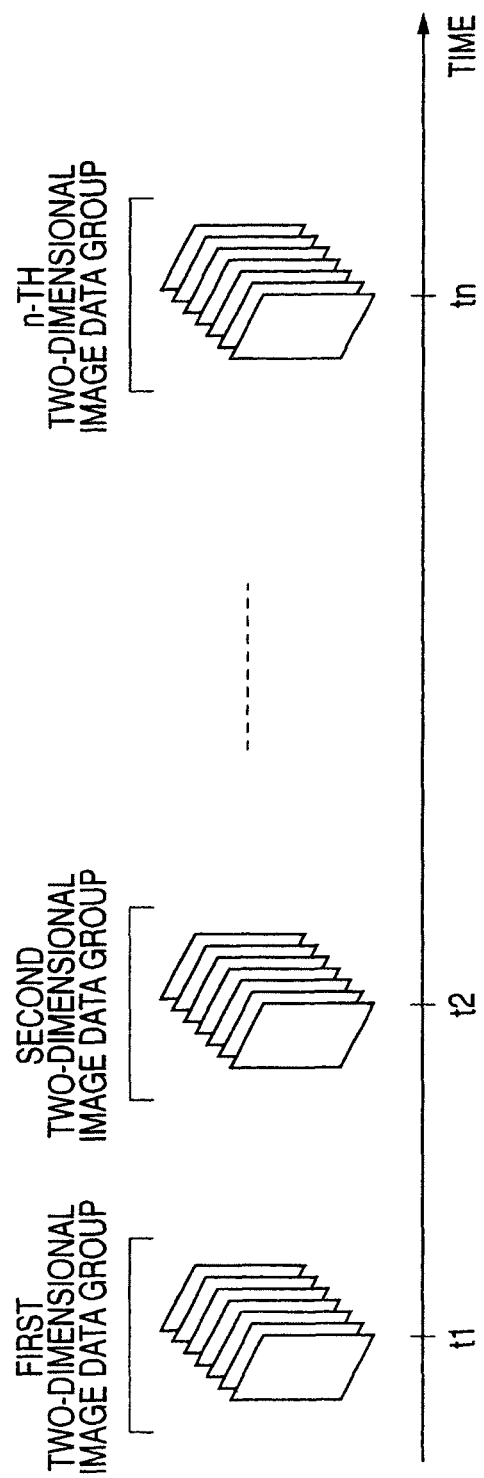
FIG. 10 is a diagram illustrating the blur correction according to the fourth embodiment of the invention.

Next, a fourth embodiment of the invention will be described below with reference to FIGS. 9 and 10.

When the ultrasonic probe deviates from an ultrasonic scanning surface (or an ultrasonic tomography or an ultrasonic image surface), the techniques described in the first to third embodiments can appropriately correct the blur of an image caused by the deviation. In the maximum brightness value holding operation, the maximum brightness value is selected from a plurality of images, and is projected onto an image. Therefore, even when the ultrasonic probe deviates in a direction (fanning direction) orthogonal to the ultrasonic scanning surface, clinical problems do not arise since information on a desired tomographic position is included in the image having the maximum brightness value projected thereon.

It is considered that a clinical value is high since the blur of an image in the fanning direction is corrected to realize the maximum brightness value holding operation using time-series image data related to the same tomographic image. In this embodiment, an ultrasonic diagnostic apparatus capable of correcting the blur of an image in the fanning direction and realizing appropriate IMF will be described below.

FIG. 9 is a flow chart illustrating the flow of MFI including the blur correction according to this embodiment. As shown in FIG. 9, when a contrast medium is injected into an object to be examined (step S40), a time-series two-dimensional image data group (which may not form volume data) on a portion to be diagnosed, which is shown in FIG. 10, is acquired (step S41). Then, standard image data is designated on the basis of the two-dimensional image data group at a time t1, and ROI for correcting blur is set according to the existing algorithm (step S42; see FIG. 4).

Subsequently, image data corresponding to the standard image data is selected from the two-dimensional image data groups collected at different times (step S43). That is, for example, it is assumed that two-dimensional image data groups corresponding to seven frames are time-serially collected in step S41 and image data corresponding to a fourth frame in the two-dimensional image data group collected at the time t1 is regarded as the standard image data. In this case, image data having the strongest correlation with the standard image data is determined from image data corresponding to a fourth frame in a second two-dimensional image data group collected at a time t2 and image data corresponding to several frames (for example, third and fifth frames) immediately before and after the image data corresponding to the fourth frame, and is selected as corresponding image data.

Then, the same process as described above is performed using a third two-dimensional image data group collected at a time t3. For example, image data corresponding to a third frame is selected as corresponding image data at the time t3. In this case, image data having the strongest correlation with the standard image data is determined from image data corresponding to a third frame in the second two-dimensional image data group collected at the time t3 and image data corresponding to several frames (for example, second and fourth frames) immediately before and after the image data corresponding to the third frame, and is selected as corresponding image data. Similarly, corresponding image data is selected from each two-dimensional image data group collected at a time t4, . . . , tn.

The method of determining the correlation is not a specific method. For example, pattern matching may be used to calculate a correlation value between the standard image data and each image to determine the correlation therebetween. When the selection of the corresponding image data at each time is performed in real time, an ultrasonic scanning area may be automatically controlled such that several frames immediately before and after the spatial position of the latest corresponding image data are collected, and the same selecting process will be performed using the obtained two-dimensional image data group.

Next, the blur correction is performed using the standard image data and the corresponding image data at each time (step S44), and a diagnostic image is generated by the maximum brightness value holding operation (step S45). The generated diagnostic image is sequentially or statically displayed on the monitor 12 in a predetermined format (step S46).

In the above-mentioned structure, image data having the strongest correlation with the standard image data is selected as corresponding image data from the image data groups collected at each time, and blur correction is performed using the corresponding image data. Therefore, even when the position of the standard image data moves in the fanning direction due to the positional deviation of the ultrasonic probe in the fanning direction, it is possible to select an image closest to the position of the standard image data before the movement as a corresponding image. The blur correction using the corresponding image according to any one of the first to third embodiments makes it possible to realize the maximum brightness value holding operation using time-series image data for the same tomography.

Fifth Embodiment

Next, a fifth embodiment of the invention will be described below. In the fifth embodiment, a correlation amount S, which is an index for generating a motion vector, is calculated, and blur correction (movement correction) is performed on the correction amount. An ultrasonic diagnostic apparatus according to this embodiment has substantially the same structure as that shown in FIG. 1. Therefore, only the components having different functions from those in the ultrasonic diagnostic apparatus shown in FIG. 1 will be described below.

A control processor 25 creates a search area on image data and moves the search area over all image data to detect the brightness of pixels included in the search area. Then, the control processor 25 sets ROI on the image data on the basis of the brightness of the pixels included in the search area. In addition, the control processor 25 calculates the correlation amounts S on the basis of the brightness of the pixels included in ROIs of a plurality of image data, and generates motion vectors indicating the movement between the image data on the basis of the obtained correlation amounts S. Subsequently, the control processor 25 performs movement correction on the image data on the basis of the motion vectors.

Next, a movement detection mode according to this embodiment of the invention will be described below.

Figure 11:
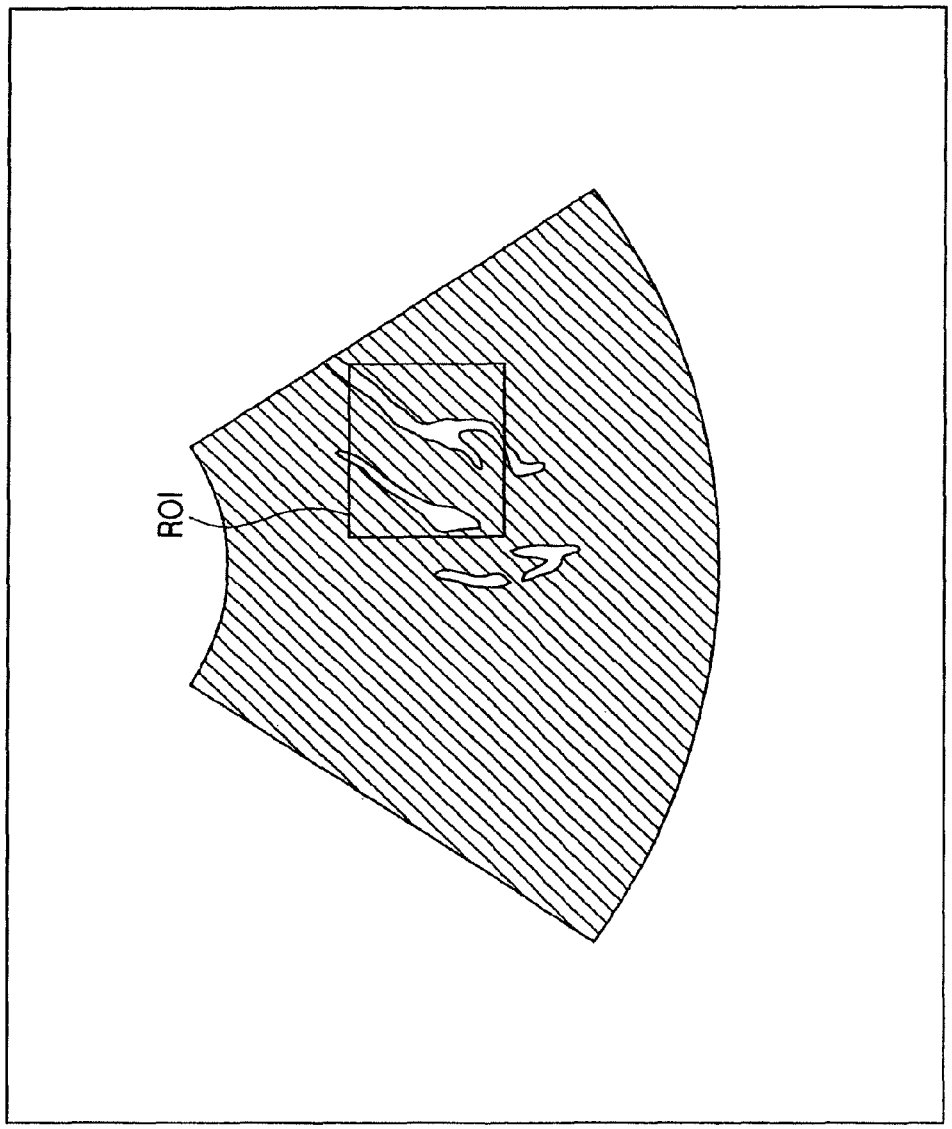
FIG. 11 is a diagram schematically illustrating a diagnostic image having an ROI mark superposed thereon according to a fifth embodiment of the invention.

First, steps S1 to S4 shown in FIG. 4 are sequentially performed to search image areas satisfying ROI conditions. When the image areas satisfying the ROI conditions are searched, an image area including the largest number of pixels having a brightness higher than K is specified among the searched image areas, and ROI is set into the specified image area. In this way, an ROI setting sequence is completed. As shown in FIG. 11, the set ROI is superposed as a rectangular ROI mark on a diagnostic image displayed on the monitor 12.

Meanwhile, when the image areas satisfying the ROI conditions are not searched on reference image data even when the search area is moved over the reference image data, the ROI setting sequence ends. When the image areas satisfying the ROI conditions are not searched and the ROI setting sequence ends, the subsequent image data is designated as the reference image data, and the ROI setting sequence is performed again. In this way, the ROI setting sequence is repeated until ROI is set.

Further, in this embodiment, ROI is automatically set, but the invention is not limited thereto. For example, ROI may be manually set by using the track ball input unit 131.

When ROI is set through the above-mentioned procedure, the next image data is designated to target image data. The target image data moves in the units of pixels in the X-axis and Y-axis directions on the basis of the position thereof at the time when it is generated. Whenever the target image data is moved by one pixel, the brightness $I(X, Y)$ of the pixels included in ROI of the reference image data and the brightness $I'(X, Y)$ of the pixels included in ROI of the target image data are extracted, and are substituted into Expression 1 given below. In this way, the correlation amounts S corresponding to the number of movements of the target image data are calculated.

When the correlation amounts S corresponding to a predetermined number of movements of the target image data are obtained, the smallest correlation amount S is searched from the obtained correction amounts S, and the amount of movement of the target image data corresponding to the smallest correlation amount S and the movement direction thereof are specified. Then, the motion vectors of the target image data are calculated on the basis of the specified movement amount and movement direction. The calculated motion vectors are stored in the image memory 30a so as to be associated with the corresponding target image data.

When the motion vectors of the target image data are obtained in this way, the display position of the target image data is corrected on the basis of the motion vectors. Then, corrected image data that little deviates from the standard image data is generated. The corrected image data is superposed on the standard image data by a maximum brightness value holding operation to generate superposed image data.

Meanwhile, when the superposed image data has already been generated, image data that is newly generated is designated to the target image data. The target image data is moved in the units of pixels in the X-axis and Y-axis directions on the basis of the position thereof at the time when it is generated. Whenever the target image data is moved by one pixel, the brightness $I(X, Y)$ of the pixels included in ROI of the superposed image data that has already been generated and the brightness $I'(X, Y)$ of the pixels included in ROI of the target image data are extracted, and are substituted into Expression 1 given below. In this way, the correlation amounts S corresponding to the number of movements of the target image data are calculated.

When the correlation amounts S corresponding to a predetermined number of movements of the target image data are obtained, the smallest correlation amount S is searched from the obtained correction amounts S, and the amount of movement of the target image data corresponding to the smallest correlation amount S and the movement direction thereof are specified. Then, the motion vectors of the target image data are calculated on the basis of the specified movement amount and movement direction. The calculated motion vectors are stored in the image memory 30a so as to be associated with the corresponding target image data.

When the motion vectors of the target image data are obtained in this way, the display position of the target image data is corrected on the basis of the motion vectors. Then, corrected image data that little deviates from the superposed image data which has already been generated is generated. The corrected image data is superposed on the superposed image data by a maximum brightness value holding operation. The superposed image data is sequentially updated through the above-mentioned procedure.

The correlation amount S is calculated by the following Expression 1:

$$s = \Sigma_X \Sigma_Y D(X,Y)$$

$$D(X,Y) = I(X,Y)_N - I'(X,Y)_{N-1} (I(X,Y)_N - I'(X,Y)_{N-1} > 0) = 0 (I(X,Y)_N - I'(X,Y)_{N-1} \leq 0).$$ [Expression 1]

Figure 12:
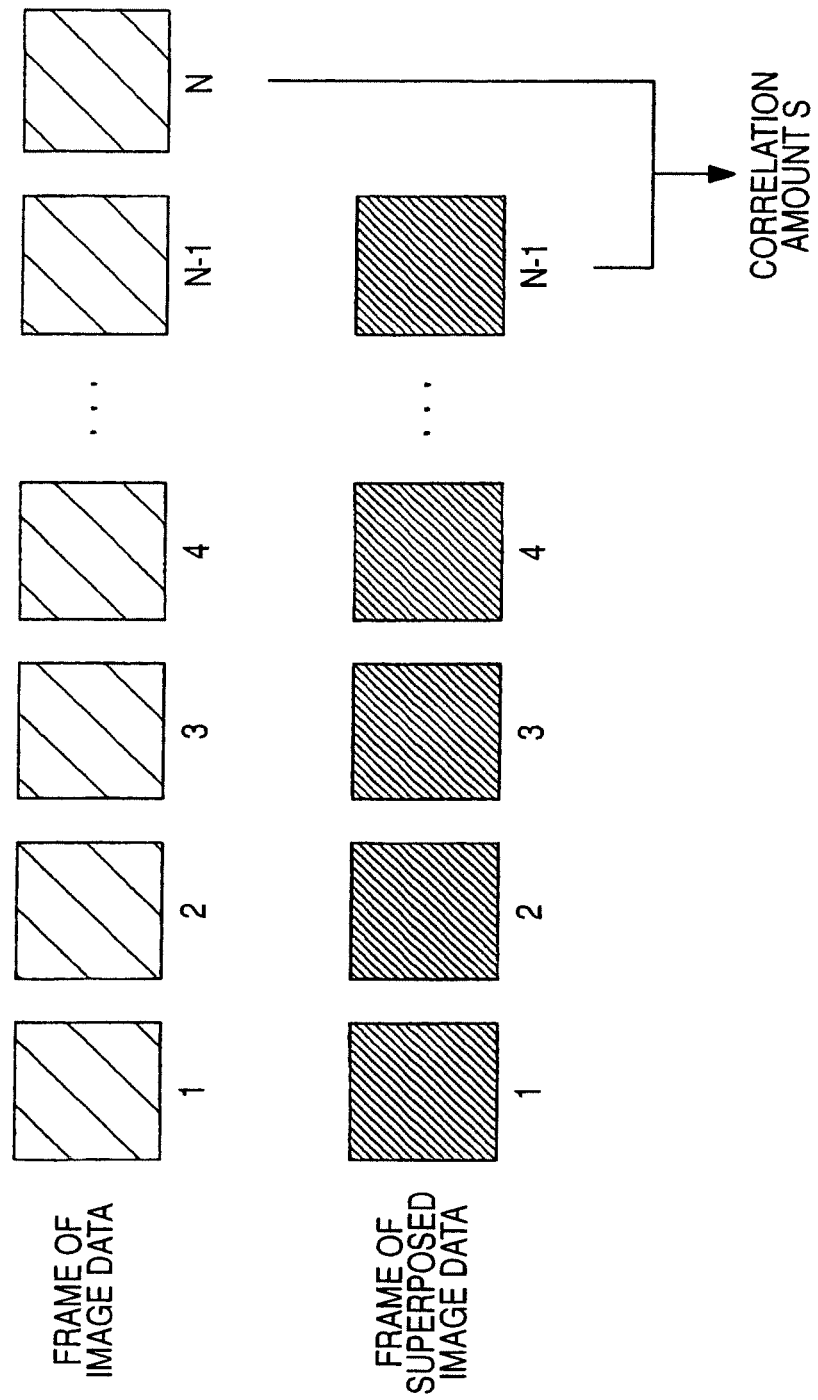
FIG. 12 is a diagram illustrating a method of calculating a correlation amount according to the fifth embodiment of the invention.

In Expression 1, a symbol 'N' indicates the frame number of image data. As shown in FIG. 12, a first frame of the image data is treated as a first frame of the superposed image data. Therefore, an (N−1)-th frame of the superposed image data is superposed on the first frame of the image data (reference image data). In this way, the second to (N−1)-th frames of the superposed image data are superposed to the corresponding frames of the image data.

As can be seen from Expression 1, the correlation amount S used in this embodiment is the total sum of brightness increments when image data that is newly generated, that is, the target image data is superposed on the superposed image data.

When the start button 132b is turned on in the movement detection mode, image data generated thereafter is sequentially corrected to generate corrected image data. When the corrected image data is generated, the corrected image data is superposed on the superposed image data by the maximum brightness value holding operation.

Therefore, while the superposition of the corrected image data is performed, the structure of blood vessels of an object to be examined is extracted on a scanning surface. Since movement correction is performed on the corrected imaged data to be superposed by a pre-process, a very clear diagnostic image is displayed on the monitor 12. Therefore, it is possible to obtain a very clear diagnostic image without being affected by the movement of an object P to be examined or the movement of an operator's hand holding the ultrasonic probe 11.

Further, in this embodiment, an example where the start button 132b is pushed during low-sound pressure scanning has been described above, but the invention is not limited thereto. For example, the start button 132b may be pushed when movement correction is performed immediately after flash. Therefore, a detailed description thereof will be omitted.

(Effects of Fifth Embodiment)

In this embodiment, the total sum of brightness increments when image data that is newly generated is superposed on the superposed image data is used as the correlation amount S serving as an index for generating motion vectors. Therefore, even when the dyed bubbles of the contrast medium appear or disappear abnormally, the dyed bubbles of the contrast medium are continuously displayed, so that motion vectors are generated. As a result, even when MFI is performed, the accuracy of motion vectors of the target image data is improved, which makes it possible to obtain a very clear diagnostic image.

In this embodiment, ROI is set to an area including a thick blood vessel having the bubbles of the contrast medium concentrated thereon. Therefore, even when there is little area serving as a mark for movement correction, for example, immediately after flash, ROI of the superposed image data is easily correlated to image data that is newly generated.

In this embodiment, the number of pixels included in ROI is smaller than the total number of pixels of image data. Therefore, the amount of calculation required to calculate the correction amount S between ROI of the superposed image data and ROI of the target image data is considerably reduced.

In this embodiment, the ROI marks superposed on the diagnostic image are displayed on the monitor 12. Therefore, the operator can check whether ROI is appropriately set from the diagnostic image displayed on the monitor 12.

In this embodiment, a movement correcting sequence starts only when ROI is set. Therefore, when there is no area serving as an index for movement correction, the target image data is not corrected.

In this embodiment, the motion vectors are stored in the image memory 30a so as to be associated with the target image data. Therefore, when the superposed image data is reconstructed on the basis of the image data having been stored in the image memory 30a, it is unnecessary to generate the motion vector, which makes it possible to generate a clear diagnostic image with a small amount of calculation.

Further, in this embodiment, MFI has been described above, but the invention is not limited thereto. That is, the invention can be applied to 'Panoramic Imaging' described in the 'Background Art' as long as a technique for superposing a plurality of image data can be used.

Furthermore, in this embodiment, the number of ROIs and the sizes thereof are input through the input device 13, but the invention is not limited thereto. For example, the number of ROIs and the sizes thereof may be automatically set on the basis of the brightness of the pixels included in the reference image data.

Moreover, in this embodiment, ROI is automatically set on the basis of the brightness of the reference image data, but the invention is not limited thereto. For example, ROI may be set so as to be operatively associated with a focal point of an ultrasonic wave transmitted by the transmitting/receiving unit 21, or it may be set according to instructions from the operators.

Further, in this embodiment, the motion vectors are stored in the image memory 30a so as to be associated with the target image data, but the invention is not limited thereto. For example, the corrected image data may be stored in the image memory 30a. In this case, it is unnecessary to correct the target image data, which makes it possible to generate a clear diagnostic image with a very small amount of calculation.

Sixth Embodiment

Figure 13:
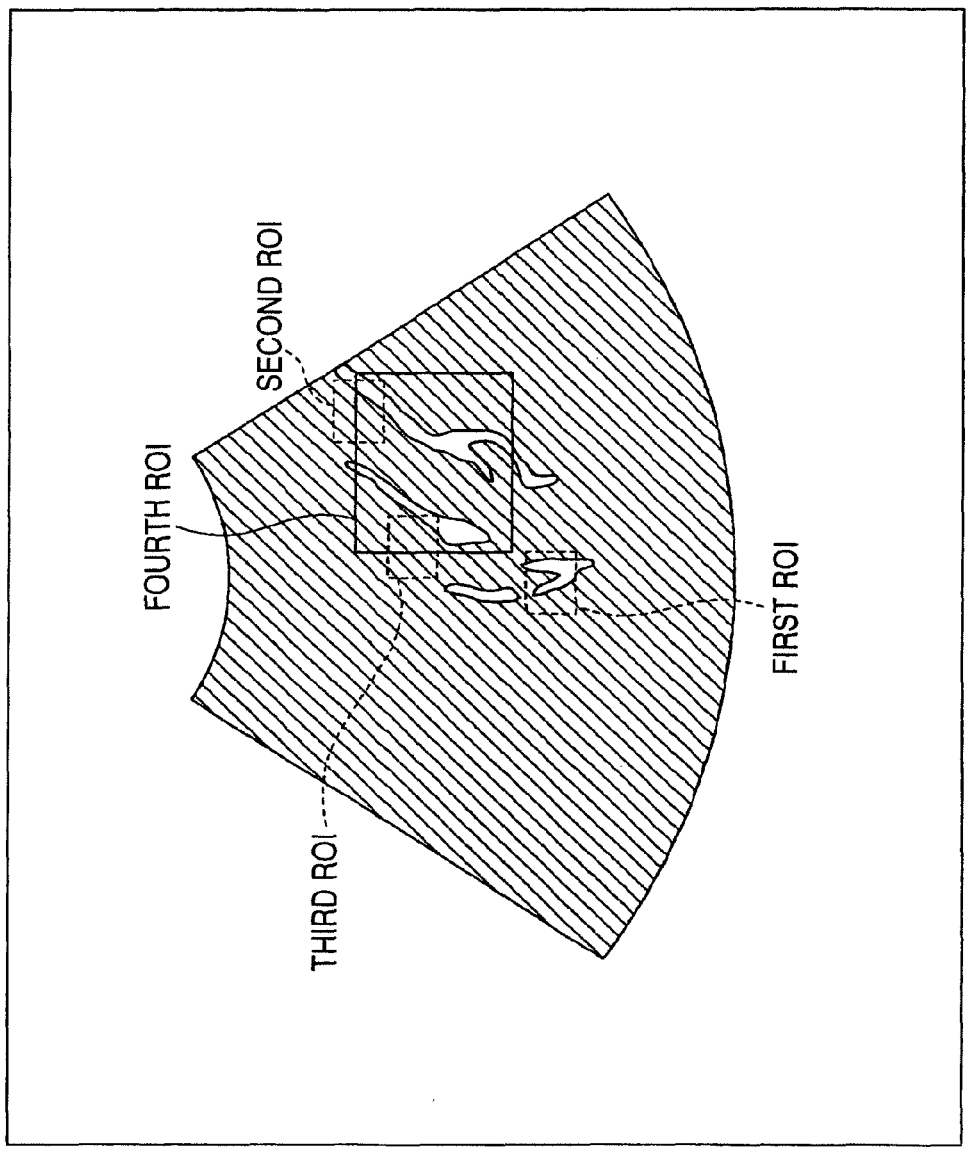
FIG. 13 is a diagram schematically illustrating a diagnostic image having ROI marks superposed thereon according to a sixth embodiment of the invention.

Next, a sixth embodiment of the invention will be described with reference to FIG. 13. FIG. 13 is a diagram schematically illustrating a diagnostic image having ROI marks superposed thereon according to the sixth embodiment of the invention.

In the sixth embodiment, as shown in FIG. 13, the control processor 25 sets first to fourth ROIs on reference image data. The fourth ROI corresponds to ROI according to the fifth embodiment. Therefore, in the sixth embodiment, the control processor 25 sets the first to third ROIs in addition to ROI according to the fifth embodiment. The sizes of the first to third ROIs are smaller than the size of the fourth ROI.

When the first to fourth ROIs are set, first to third motion vectors indicating the movement of target image data are calculated on the basis of a correlation amount S' between the first to third ROIs of the target image data and the first to third ROIs of the superposed image data. In this embodiment, SAD is used as the correlation amount S'.

When the first to third motion vectors are calculated, the target image data is moved on the basis of the first to third motion vectors. Whenever the target image data is moved, the first to third correlation amounts S are calculated on the basis of the fourth ROI of the superposed image data and the fourth ROI of the target image data by Expression 1, similar to the fifth embodiment.

When the first to third correlation amounts S are calculated, the smallest correlation amount S is detected from the first to third correlation amounts S, and a vector of the target image data corresponding to the smallest correlation amount is used as the motion vector. Then, the display position of the target image data is corrected on the basis of the motion vector.

As described above, in this embodiment, the motion vector is selected from the first to third vectors that are acquired beforehand. That is, only three calculating processes are needed to generate the motion vector (calculating processes using Expression 1). Therefore, it is possible to considerably reduce the amount of calculation required to calculate the motion vector, as compared to the fifth embodiment. In addition, even when the motion vector varies with parts of the object to be examined, the accuracy of the motion vector is not excessively lowered.

In this embodiment, a so-call SAD is used as the correlation amount S', but the invention is not limited thereto. That is, the correlation amount S' may be calculated by Expression 1. The use of Expression 1 also makes it possible to reduce the amount of calculation, since the sizes of the first to third ROIs are smaller than that of the fourth ROI.

Further, in this embodiment, the motion vector is calculated by Expression 1 on the basis of the first to third motion vectors that are obtained beforehand, but the invention is not limited thereto. For example, the motion vector may be the mode value or the average value of the first to third motion vectors. The use of the mode value or the average value makes it possible to reduce the amount of calculation.

Seventh Embodiment

In a seventh embodiment of the invention, a zero vector is used in addition to the first to third vectors used in the sixth embodiment. That is, in this embodiment, even when the target image data does not move, the fourth correlation amount S is calculated by Expression 1 on the basis of the fourth ROI of the target image data and the fourth ROI of the superposed image data that has already been generated or the fourth ROI of the reference image data, similar to the fifth embodiment.

When the first to fourth correlation amounts S are calculated, the smallest correlation amount S is detected from the first to fourth correlation amounts S, and a vector of the target image data corresponding to the smallest correlation amount is used as the motion vector. Then, the display position of the target image data is corrected on the basis of the motion vector.

As described above, in this embodiment, even when the target image data does not move, the fourth correlation amount S is calculated by Expression 1. Therefore, even when the ultrasonic probe 11 is inclined to the lens to cause the first and third vectors to vary, the accuracy of the motion vector that is actually used is not excessively lowered.

Eighth Embodiment

In an eighth embodiment of the invention, it is assumed that three-dimensional image data is generated. Therefore, a three-dimensional ROI is set on reference image data. When the three-dimensional ROI is used, the amount of calculation required to calculate the correlation amount S is considerably increased.

For the reason, in this embodiment, first to third two-dimensional ROIs are used instead of the three-dimensional ROI. The first to third ROIs are included in the three-dimensional ROI and are orthogonal to one another. In addition, the first to third ROIs are generated as MPR of the third-dimensional ROI. The first to third ROIs used in the eighth embodiment are different from the first to third ROIs used in the sixth or seventh embodiment.

When the first to third ROIs are generated, first to third vectors respectively corresponding to the first to third ROIs are generated by the same method as that in the fifth embodiment. The first to third vectors used in the eighth embodiment are different from the first to third vectors used in the sixth or seventh embodiment.

When the first to third vectors are generated, a third-dimensional motion vector that is actually used to correct the movement of the target image data is generated on the basis of the first to third vectors.

As described above, in this embodiment, the first to third two-dimensional ROIs are used instead of the three-dimensional ROI. Therefore, even when three-dimensional image data is generated, the amount of calculation required to calculate the correlation amount S is considerably decreased.

Further, in this embodiment, the third-dimensional motion vector is generated on the basis of the first to third vectors, and then the target image data is corrected. However, the invention is not limited thereto. For example, the target image data may be corrected for each of the first to third vectors. In this case, three correcting processes are needed, and it is not necessary to generate the motion vector.

Ninth Embodiment

In a ninth embodiment of the invention, the control processor 25 detects the sum of brightnesses of the pixels included in ROI of the superposed image data. When the sum of brightnesses is larger than a predetermined value, the control processor 25 stops correcting the movement of the target image data. Therefore, even when a plurality of image data are superposed on each other and ROI of the superposed image data has an excessively high brightness, the accuracy of the motion vector is not excessively lowered.

Tenth Embodiment

In a tenth embodiment of the invention, it is assumed that both bloodstream image data and tissue image data are displayed. The bloodstream image data corresponds to the image data in each of the above-described embodiments. The tissue image data does not vary over time unlike the bloodstream image data, which makes it easy to calculate the motion vector. Therefore, in this embodiment, ROI is set to the tissue image data, and the motion vector is generated by Expression 1 in the same manner as that in the first embodiment. Then, the movement of only the bloodstream image data is corrected on the basis of the generated motion vector.

When the movement of the bloodstream image data is corrected on the basis of ROI set to the tissue image data as in the tenth embodiment, a more clear diagnostic image is obtained. In addition, in this embodiment, the tissue image data is displayed on the monitor 12 without being corrected. Therefore, the tissue image data displayed on the monitor 12 makes it easy for the operator to check the movement and to view the state of the object P to be examined. As a result, the operator can perform a medical examination with confidence.

Eleventh Embodiment

FIGS. 14, 15, 16, and 17 are diagrams illustrating the correction results of image data superposed on a diagnostic image according to an eleventh embodiment of the invention. In the eleventh embodiment, the correction result of the target image data is superposed on the diagnostic image. The correction results are displayed in several types as shown in FIGS. 14, 15, 16, and 17.

Figure 14:
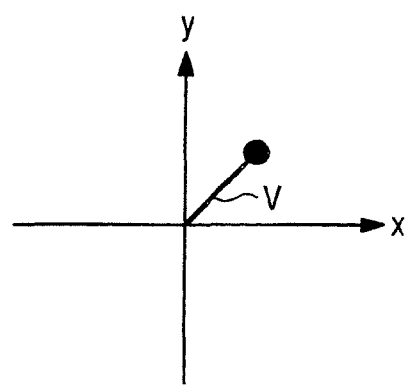
FIG. 14 is a diagram schematically illustrating an example of the correction result of image data superposed on a diagnostic image according to an eleventh embodiment of the invention.
Figure 15:
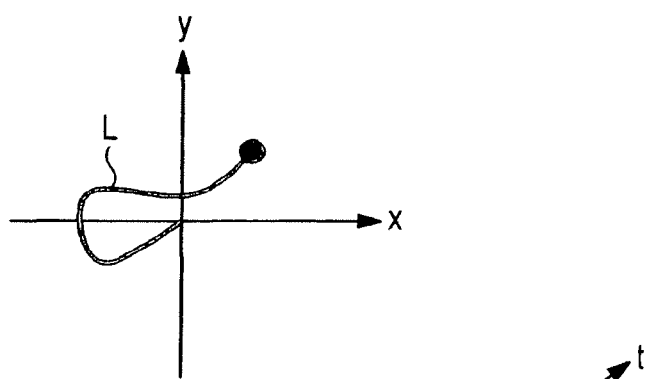
FIG. 15 is a diagram schematically illustrating an example of the correction result of image data superposed on a diagnostic image according to the eleventh embodiment of the invention.
Figure 16:
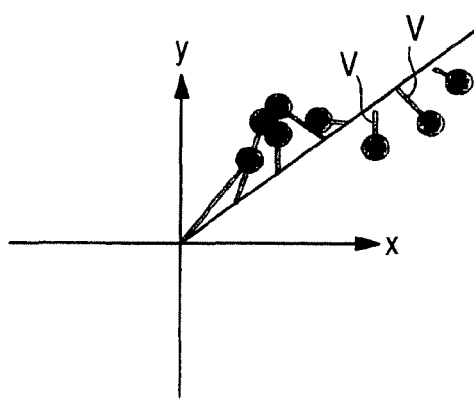
FIG. 16 is a diagram schematically illustrating an example of the correction result of image data superposed on a diagnostic image according to the eleventh embodiment of the invention.
Figure 17:
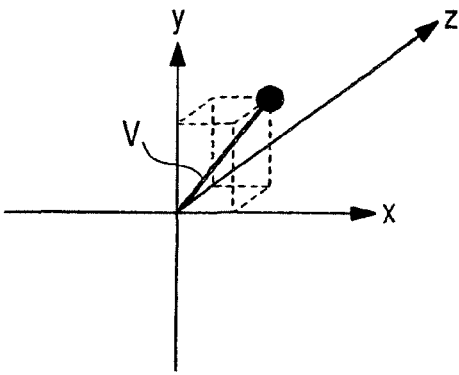
FIG. 17 is a diagram schematically illustrating an example of the correction result of image data superposed on a diagnostic image according to the eleventh embodiment of the invention.

As shown in FIG. 14, only a motion vector V of the target image data is displayed as the correction result of the target image data. Therefore, it is very easy to confirm the correction result of the target image data in a moment. As shown in FIG. 15, a locus L of an end point of the motion vector V is displayed as the correction result of the target image data. Therefore, it is very easy to know a change in the motion vector V over time. As shown in FIG. 16, a plurality of motion vectors V that are sequentially generated are displayed as the correction result of the target image data, similar to FIG. 14, but a time axis t is added to an X-axis and a Y-axis. FIG. 17 shows the correction result of three-dimensional volume data. As shown in FIG. 17, only the motion vector V of the target image data is displayed, similar to FIG. 14.

As described above, when the correction result is superposed on the diagnostic image displayed on the monitor 12, the operator can easily confirm the correction result and use a correcting function with confidence.

Twelfth Embodiment

A twelfth embodiment of the invention relates to an application of the acquired motion vector. For example, the acquired motion vector is used to move a range gate of a pulse wave. In this case, when the range gate of pulsed-wave Doppler is set in a desired blood vessel, it is possible to continuously acquire signals from the desired blood vessel even when the object P to be examined or the ultrasonic probe 11 moves a little. The motion vector is used to correct the position of a color ROI, to maintain the same cross section of an object to be examined, and to follow an interesting area by using brightness analyzing software, in addition to moving the range gate of pulse-wave Doppler.

Conversely, when a background image is corrected with the range gate of the pulse wave or the position of the color ROI being fixed, the operator can view a diagnostic image including an interesting area. This is very useful to observe a variation in brightness over time or to analyze a diagnostic image.

The invention is not limited to the above-described embodiments, but various modifications and changes of the invention can be made without departing from the scope and spirit of the invention. A plurality of components described in the embodiments may be appropriately combined with each other to form various modifications. For example, some components may be removed from all the components in the above-described embodiments. In addition, different components in the above-described embodiments may be combined with each other.

According to the present invention, it is possible to provide an ultrasonic diagnostic apparatus and an ultrasonic image generating method capable of preventing the quality of an image from being lowered even when an object to be examined or an ultrasonic probe moves a little.

What is claimed is:

1. An ultrasonic diagnostic apparatus that scans an object to be examined, into which a contrast medium is injected, with ultrasonic waves to acquire an ultrasonic image of the object, the apparatus comprising:
    an ultrasonic probe configured to repeatedly transmit the ultrasonic waves to the object and acquire echo signals returning from the object, the ultrasonic probe being held by a user;
    an image generating circuit configured to generate a plurality of time-series two-dimensional images of a region in the object on the basis of the echo signals, the plurality of time-series two-dimensional images being collected with a position of the ultrasonic probe kept still;
    a control processor including a CPU executing a program, the control processor being configured to select, from the time-series two-dimensional images, a first image corresponding to a time point at which an amount of the contrast medium flows into the region, by analyzing the time-series two-dimensional images;
    set, in the first image, a first interesting area depicting a structure of a blood vessel dyed with the amount of the contrast medium by analyzing the first image,
    set a search area in a second image which is collected after the first image, the second image being included in the plurality of time-series two-dimensional images;
    move the search area in the second image;
    determine a second interesting area corresponding to the first interesting area in the second image based on brightness values included in the moved search area;
    generate a motion vector which indicates a motion between the first image and the second image, based on positions of the first interesting area and the second interesting area;
    correct a blur between the first and the second images on the basis of the motion vector; and
    generate a display image by performing a brightness value holding operation after the correcting of the blur between the first and second images, wherein the brightness value holding operation includes selecting, for each pixel location independently, a maximum brightness value among corresponding brightness values at the pixel location in the first and second images, and setting a brightness value at the pixel location in the display image to the selected maximum brightness value; and
    a monitor configured to display the display image generated by performing the brightness value holding operation after the correcting of the blur between the first and second images.

2. The ultrasonic diagnostic apparatus according to claim 1, wherein the control processor is further configured to detect a time when the amount of the contrast medium flows into the region in the object.

3. The ultrasonic diagnostic apparatus according to claim 1, wherein the control processor is further configured to set a first search area in the first image, move the first search area across the entire first image, and select a first search area which includes the most number of positions having brightness values larger than a predetermined threshold value to determine the first interesting area.

4. The ultrasonic diagnostic apparatus according to claim 3, wherein the control processor is further configured to make a histogram related to the brightness values of the first image, and determine the predetermined threshold value on the basis of the histogram.

5. The ultrasonic diagnostic apparatus according to claim 1, wherein the control processor is further configured to set a first search area in the first image, move the first search area across the entire first image, and select a first search area which includes the most number of positions between a first predetermined threshold value and a second predetermined threshold value.

6. The ultrasonic diagnostic apparatus according to claim 5, wherein the control processor is further configured to make a histogram related to the brightness values of the first image, and determine at least one of the first threshold value and the second threshold value on the basis of the histogram.

7. The ultrasonic diagnostic apparatus according to claim 1,
wherein the control processor is further configured to determine at least one of a position, size, and shape of the first interesting area and a number of first interesting areas on the basis of brightness at each position on the first image.

8. The ultrasonic diagnostic apparatus according to claim 1,
wherein, whenever the control processor is further configured to generate the image, the control processor is further configured to update the second interesting area on the basis of another second interesting area used to correct blur of a previous image and a resultant vector of a plurality of motion vectors that have been generated by the control processor.

9. The ultrasonic diagnostic apparatus according to claim 1,
wherein the control processor is further configured to determine the second interesting area in the second image based on correlation between the brightness values included in the search area in the second image and brightness values included in a search area in a previous second image.

10. The ultrasonic diagnostic apparatus according to claim 1,
wherein the control processor is further configured to determine the second interesting area in each second image based on a correlation between the brightness values included in each moved search area and the brightness values included in the first interesting area.

11. The ultrasonic diagnostic apparatus according to claim 1,
wherein the ultrasonic probe is further configured to perform first ultrasonic transmission at a first sound pressure that breaks the contrast medium bubbles and second ultrasonic transmission at a second sound pressure for imaging reflux of a bloodstream at which the contrast medium bubbles are not broken, and
the control processor is further configured to designate that an image generated immediately after the first ultrasonic transmission is switched to the second ultrasonic transmission as the first image.

12. The ultrasonic diagnostic apparatus according to claim 1,
wherein the ultrasonic probe is further configured to perform first ultrasonic transmission at a first sound pressure that breaks the contrast medium bubbles and second ultrasonic transmission at a second sound pressure for imaging reflux of a bloodstream at which the contrast medium bubbles are not broken, and
the control processor is further configured to set the first interesting area in the first image in response to the switching of the first ultrasonic transmission to the second ultrasonic transmission.

13. The ultrasonic diagnostic apparatus according to claim 1,
wherein the control processor is further configured to generate a first display image based on the plurality of images after the blur correction, and generate a second display image on the basis of the plurality of images before the blur correction, and
the monitor simultaneously or selectively displays the first display image and the second display image.

14. The ultrasonic diagnostic apparatus according to claim 1,
wherein the control processor is further configured to generate a resultant vector by using a plurality of motion vectors; and
the control processor is further configured to correct the blur of the first image and a subsequent image on the basis of the resultant vector.

15. The ultrasonic diagnostic apparatus according to claim 14,
wherein the control processor is further configured to generate a subsequent motion vector between a superimposed image generated by superimposing the plurality of the images and the subsequent image; and
the control processor is further configured to correct the blur of the subsequent image and the subsequent image on the basis of the subsequent motion vector.

16. The ultrasonic diagnostic apparatus according to claim 15,
wherein the control processor is further configured to generate the subsequent motion vector on the basis of brightness values of a second interesting area of the superimposed image and brightness values of a second interesting area of the subsequent image.

17. The ultrasonic diagnostic apparatus according to claim 16,
wherein the control processor is further configured to generate the subsequent motion vector in such a manner that a sum of the brightness values of the second interesting area of the superimposed image and the brightness values of the second interesting area of the subsequent image is a maximum value.

18. The ultrasonic diagnostic apparatus according to claim 16,
wherein, when a sum of the brightness values of the second interesting area of the superimposed image and the brightness values of the second interesting area of the subsequent image is larger than a predetermined value, the control processor is configured to stop correcting blur of the subsequent image.

19. The ultrasonic diagnostic apparatus according to claim 14,
wherein the control processor is further configured to correct the blur of the subsequent image, and maintain a displayed area of the object to be examined on a diagnostic image.

20. The ultrasonic diagnostic apparatus according to claim 14, wherein the control processor is further configured to:
correct a position of a range gate in pulsed-wave Doppler on the basis of the motion vector generated by the control processor.

21. The ultrasonic diagnostic apparatus according to claim 14,
wherein the plurality of images include bloodstream images and tissue images.

22. A method of generating an ultrasonic diagnostic image by scanning an object to be examined into which a contrast medium is injected with ultrasonic waves, the method comprising:
repeatedly transmitting the ultrasonic waves to the object with an ultrasonic probe held by a user and generating a plurality of time-series two-dimensional images of a region in the object on the basis of echo signals returning from the object, the plurality of time-series two-dimensional images being collected with a position of the ultrasonic probe kept still;

selecting, from the time-series two-dimensional images, a first image corresponding to a time point at which an amount of the contrast medium flows into the region, by analyzing the time-series two-dimensional images;

setting, in the first image, a first interesting area depicting a structure of a blood vessel dyed with the amount of the contrast medium by analyzing the first image;

setting a search area in a second image that is collected after the first image, the second image being included in the plurality of time-series two-dimensional images;

moving the search area in the second image;

determining a second interesting area corresponding to the first interesting area in the second image based on brightness values included in the moved search area;

generating, by processing circuitry, a motion vector, which indicates a motion between the first image and the second image, based on positions of the first interesting area and the second interesting area;

correcting, by the processing circuitry, a blur between the first and the second images on the basis of the motion vector;

generating a display image by performing a brightness value holding operation after the correcting of the blur between the first and second images, wherein the brightness value holding operation includes selecting, for each pixel location independently, a maximum brightness value among corresponding brightness values at the pixel location in the first and second images, and setting a brightness value at the pixel location in the display image to the selected maximum brightness value; and displaying, on a monitor, the display image generated by performing the brightness value holding operation after the correcting of the blur between the first and second images.

23. The ultrasonic diagnostic apparatus of claim 1, wherein the control processor is further configured to set the search area, which has a same size and shape as the first interesting area.

* * * * *